(12) United States Patent
Laskin et al.

(10) Patent No.: US 8,343,971 B2
(45) Date of Patent: Jan. 1, 2013

(54) PHARMACOLOGICALLY-ACTIVE VANILLOID CARBAMATES

(75) Inventors: Jeffrey D. Laskin, Piscataway, NJ (US); Diane E. Heck, Rumson, NJ (US); Carl Jeffrey Lacey, Schnecksville, PA (US); Erik Aponte, Pine Bush, NY (US); Mou-Tuan Huang, Englewood Cliffs, NJ (US); Ned D. Heindel, Easton, PA (US)

(73) Assignees: Rutgers, The State University of New Jersey, New Brunswick, NJ (US); The University of Medicine and Dentistry of New Jersey, Somerset, NJ (US); Lehigh University, Bethlehem, PA (US)

( * ) Notice: Subject to any disclaimer, the term of this patent is extended or adjusted under 35 U.S.C. 154(b) by 0 days.

(21) Appl. No.: 12/882,351

(22) Filed: Sep. 15, 2010

(65) Prior Publication Data

US 2012/0059007 A1    Mar. 8, 2012

Related U.S. Application Data

(60) Provisional application No. 61/276,722, filed on Sep. 15, 2009.

(51) Int. Cl.
 *A61K 31/535* (2006.01)
 *C07D 295/18* (2006.01)
(52) U.S. Cl. ................ 514/237.8; 544/168
(58) Field of Classification Search .......... 514/237.8; 544/168
 See application file for complete search history.

(56) References Cited

U.S. PATENT DOCUMENTS 6,187,754 B1 * 2/2001 Oehrlein .................... 514/25

* cited by examiner

*Primary Examiner* — Rebecca Anderson
(74) *Attorney, Agent, or Firm* — Fox Rothschild LLP

(57) ABSTRACT

This application relates to pharmacologically-active vanilloid compounds which are useful for the treatment of various anti-inflammatory states characterized by inhibition of FAAH, such as, Alzheimer's dementia, Parkinson's disease, depression, pain, rheumatoid arthritis, pathophysiology of mood disorders, multiple sclerosis, and inflammation, or antagonism of TRPV1, such as, for example, Huntington's disease, hypertension, arthritis, allergic airway inflammation, Crohn's disease, ulcerative colitis, and neuropathic pain.

11 Claims, No Drawings

PHARMACOLOGICALLY-ACTIVE VANILLOID CARBAMATES

This application claims the benefit of U.S. Provisional Ser. No. 61/276,722, filed Sep. 9, 2009, incorporated herein in its entirety.

Inflammatory processes, often amenable to address by oral or topical steroidal and non-steroidal anti-inflammatory drugs (NSAIDs such as diclofenac, ibuprofen, naproxen, and indomethacin), are inherent in the pathologies of many topical dysfunctions and systemic diseases. These include, but are not limited to dermal abrasions, psoriasis, insect bites, burns, blisters, arthritis, multiple sclerosis, Alzheimer's disease, depression, amyotrophic lateral sclerosis, dementia, Parkinson's disease, and other neurodegenerative states. On a pharmacological level, two of several targets possess validated screening links to alleviating many of the indicated inflammatory clinical conditions. These are inhibition of the enzyme fatty acid amide hydrolase (FAAH) and antagonism of the TRPV1 ion channel receptor.

FAAH was known as anandamide amidohydrolase or as oleamide hydrolase in early studies. It hydrolyzes amide-like carbonyls in fatty constructs (endogenous substrates include oleamide and anandamide) and can be inhibited by structural mimics of these same fatty amides. Physiologically, the inhibition of fatty acid amide hydrolase in vivo has the effect of blocking the hydrolytic degradation of endocannabinoids and thereby raising or maintaining the concentration of the natural cannabinoid ligands which are thought to bind to and modulate (antagonize or agonize) cannabinoid receptors such as the CB1 and CB2 receptors. A sample of the many physiological effects that can be observed by modulation of the CB1 and CB2 receptors includes regulation of colonic propulsion and intestinal transit time, suppression of pain, reduction of inflammation, modulation of the immune system, neuroprotection, appetite control, and regulation of mood disorders. Among other structures, alkyl carbamates are known to be potent inhibitors of FAAH and candidate therapeutics for inflammatory processes and associated pain. As examples these anti-inflammatories can be amides, ureas, thioamides, hydrazides, simple alkyl carbamates or bi-functional carbamates linked to classic anti-pyretics and non-steroidal anti-inflammatory drugs (NSAIDs) (M. Abouabdellah et al., 2007, O. Dasse, 2008).

FAAH has been isolated, the gene encoding it has been cloned, sequenced, and employed to express a recombinant form which has been used to screen candidate inhibitors as soporific drugs. Recently, the inhibition of FAAH has also been implicated as a pre-screen for pharmaceuticals for pain suppression, neuropsychiatric disorders, and anti-inflammatory effects (N. B. Gilula, et al., 2008; D. M. Lambert et al., 2005; B. F. Cravatt et al., 2001; D. L. Boger, 2002; O. Dasse, 2008)

Another binding target which is also closely linked to modulation of pain and inflammatory responses, is the transient receptor potential vanilloid (TRPV1) also known as the VR1 or the vanilloid/capsaicin receptor. The latter names derive from the fact that TRPV1 binds both the heat-producing component of pepper (capsaicin) as well as a family of fatty amides carrying the 4-hydroxy-3-methoxybenzylamine (vanilloid) moiety. TRPV1 is a non-selective cation channel gated by extracellular protons, heat, and small molecule amides, thioamides, and ureas containing the 4-hydroxy-3-methoxybenzyl fragment or a pro-drug form of the same entity (A. Messeguer, et al., 2006). In human skin, the dermis and the epidermis are rich with TRPV1 positive cells and in patients who have experienced painful inflammatory disorders, there is often a marked up-regulation of TRPV1 (A. Guo et al., 1999; D. N. Cortright et al., 2009).

Unlike traditional analgesic drugs that either suppress inflammation (e.g., NSAIDs and COX-2 inhibitors) or block pain transmission (e.g., opiates), TRPV1 channel inhibitors aim to prevent pain and inflammation by blocking a receptor where these adversities are generated. It is interesting that while both TRPV1 agonists and antagonists can provide pain relief and resistance to inflammatory stimuli, most of the emerging drug candidates are in fact antagonists (L. S. Premkumar et al., 2000; K. M. Walker et al., 2003). TRPV1 has been hailed as a promising new screening target for clinically effective analgesic anti-inflammatories (A. Szallasi et al., 2004).

Clinical responses are definitely modulated by the combined effects of the TRPV1 receptor and FAAH, but not in a readily predictable fashion. The pain-suppressing anti-inflammatory endogenous cannabinoids (e.g. anandamides or AEAs which bind to the CB receptors) do activate TRPV1 and they are metabolically deactivated by FAAH. Thus, in the simplest sense, one might suspect that FAAH inhibitors would elevate the concentrations of the endocannabinoids and provide therapeutic relief. In most cases, this is true with fatty acid amides showing the ability to suppress pain and inflammation arising in the carrageenan inflamed mouse paw model (J. A. Richardson, 1998). However, the reality is that anandamide and analogs can sometimes show concentration-dependent opposing effects at CB and TRPV1 receptors. For this reason, they have been referred to as "Janus-like" molecules (Lambert, 2005) and because many endocannabinoids also bind to TRPV1, van der Stelt has even suggested they be renamed "endo-vanilloids" (van der Stelt, 2004). One histocytochemical study in a particular cell type (amacrine cells) showed that TRPV1 and FAAH "co-localize" on the cell membrane. The authors suggest that because of this co-localization TRPV1 and FAAH collaboratively provide an "auto-regulatory function for anandamide," (S. Zimov et al., 2007).

In reality, FAAH inhibitory compounds can enhance, suppress, or have no effect on TRPV1 activation by anandamide depending on the specific organ and disease state being addressed (R. A. Ross, 2003). The situation is further complicated by the fact that TRPV1 expression levels can be up-regulated in some disease states. Furthermore, the candidate FAAH inhibitors being tested may themselves activate or deactivate TRPV1 (J. Ahluwalia et al., 2003). At present, the pattern of responses of TRPV1 and FAAH to candidate anti-inflammatory compounds must be experimentally correlated to an in vivo anti-inflammatory assay, such as the mouse ear inflammation model or the carrageenan inflamed paw screen, before one can assess the predictability of clinical responses by these ex vivo tests. Despite the complexities of these interactions, the use of FAAH and TRPV1 screens to determine candidate anti-inflammatories is well established (C. J. Fowler et al., 2009; A. Messeguer et al., 2006; D. M. Lambert et al., 2005).

Certain types of carbamates have been recognized as especially good inhibitors of FAAH (O. Dasse, 2008; S. Vandevoorde, 2008). Carbamates possessing at least one hydrogen on a nitrogen appear to metabolize through a highly electrophilic isocyanate, while carbamates with no hydrogens on nitrogen metabolize by a slower direct carbamoyl-group transfer (WHO 1986).

This application relates to compounds of Formula 1:

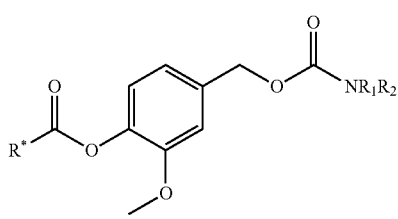

Formula 1 wherein $R_1$, $R_2$, and R* are hydrogen, $(C_1-C_{15})$alkyl, $(C_1-C_{15})$alkyl $(C_1-C_6)$alkoxy, aryl, $(C_3-C_6)$cycloalkyl, $(C_3-C_6)$cycloalkyl-$(C_1-C_6)$alkyl, $(C_1-C_6)$alkaryl, heterocyclic, $(C_1-C_6)$alkyl heterocyclic, and amino acyl and pharmaceutically acceptable addition salts thereof and optical and geometric isomers or racemic mixtures thereof;

which compounds are useful for the treatment of various anti-inflammatory states characterized by inhibition of FAAH, such as, Alzheimer's dementia, Parkinson's disease, depression, pain, rheumatoid arthritis, pathophysiology of mood disorders, multiple sclerosis, and inflammation, or antagonism of TRPV1, such as, for example, Huntington's disease, hypertension, arthritis, allergic airway inflammation, Crohn's disease, ulcerative colitis, and neuropathic pain.

Unless otherwise stated or indicated, the following definitions shall apply through the specification and the appended claims.

The term $(C_1-C_6)$alkyl or $(C_1-C_{10})$alkyl shall mean a straight or branched alkyl group, for example, methyl, ethyl, n-propyl, isopropyl, n-butyl, iso-butyl, sec-butyl, t-butyl and straight and branched chain pentyl, hexyl, heptyl, decyl, dodecyl and the like.

The term heterocyclic shall mean a cyclic substituent containing 1 or 2 heteroatoms selected from the group of nitrogen, oxygen or sulfur, for example morpholino or Throughout the specification and the appended claims, a given chemical formula or name shall encompass all stereo, optical, enantiomeric and tautomeric isomers where such isomers exists.

In one class of compounds of this invention are compounds of the formula (I)

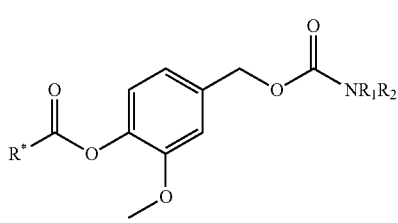

(I)

wherein $R_1$, $R_2$, and R* are hydrogen, $(C_1-C_{15})$alkyl, $(C_1-C_{15})$alkyl $(C_1-C_6)$alkoxy, aryl, $(C_3-C_6)$cycloalkyl, $(C_3-C_6)$cycloalkyl-$(C_1-C_6)$alkyl, $(C_1-C_6)$alkaryl, heterocyclic, $(C_1-C_6)$alkyl heterocyclic, and amino acyl and pharmaceutically acceptable addition salts thereof and optical and geometric isomers or racemic mixtures thereof.

In a preferred embodiment of this invention are compounds of the formula (I)

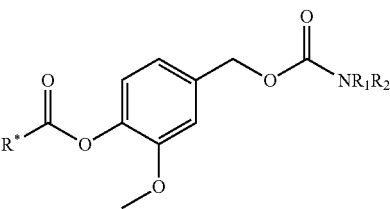

(I)

wherein $R_1$ and $R_2$ are alike or different and selected from hydrogen, $(C_1-C_{15})$alkyl, $(C_1-C_{15})$alkyl$(C_1-C_6)$alkoxy, aryl, $(C_3-C_6)$cycloalkyl, $(C_3-C_6)$cycloalkyl-$(C_1-C_6)$alkyl, $(C_1-C_6)$alkaryl, heterocyclic, $(C_1-C_6)$alkyl heterocyclic, and amino acyl;

R* is $(C_1-C_6)$alkyl or aryl; and pharmaceutically acceptable acid addition salts thereof and optical and geometric isomers or racemic mixtures thereof.

Preferably, $R_1$ is hydrogen or $(C_1-C_{15})$alkyl;

$R_2$ is hydrogen, $(C_1-C_{15})$alkyl, $(C_1-C_{15})$alkyl$(C_1-C_6)$ alkoxy, aryl, $(C_3-C_6)$cycloalkyl, $(C_3-C_6)$cycloalkyl-$(C_1-C_6)$ alkyl, $(C_1-C_6)$alkaryl, heterocyclic, $(C_1-C_6)$alkyl heterocyclic, and amino acyl; and R* is $(C_1-C_6)$alkyl, Most preferably, $R_1$ is hydrogen or n-butyl;

$R_2$ is ethyl, n-butyl, n-hexyl, n-octyl, n-heptyl, 2-ethylhexyl, n-dodecyl, cyclohexyl, cyclohexylmethyl, 2-phenoxyethyl, phenethyl, 2-indanyl, 2-methoxyethyl, 3,3-dmethylbutyl, 2-(4-morpholino)ethyl, ethyl 2-glycinyl or ethyl 2-valinyl; and R* is methyl.

Nonlimiting examples of compounds of this invention include:

4-{[(cyclohexylcarbamoyl)oxy]methyl}-2-methoxyphenyl acetate

4-{[(butylcarbamoyl)oxy]methyl}-2-methoxyphenyl acetate

4-{[(hexylcarbamoyl)oxy]methyl}-2-methoxyphenyl acetate

4-{[(octylcarbamoyl)oxy]methyl}-2-methoxyphenyl acetate

4-{[(decylcarbamoyl)oxy]methyl}-2-methoxyphenyl acetate 2-methoxy-4-({[(2-methoxyethyl)carbamoyl]oxy}methyl) phenyl acetate 4-(acetyloxy)-3-methoxybenzyl 2-thioxo-1,3-thiazolidine-3-carboxylate 4-{[(heptylcarbamoyl)oxy]methyl}-2-methoxyphenyl acetate 4-{[(dibutylcarbamoyl)oxy]methyl}-2-methoxyphenyl acetate 4-{[(benzylcarbamoyl)oxy]methyl}-2-methoxyphenyl acetate 4-{[(2-ethylhexylcarbamoyl)oxy]methyl}-2-methoxyphenyl acetate 4-{[(dodecylcarbamoyl)oxy]methyl}-2-methoxyphenyl acetate 2-methoxy-4-({[(2-phenoxyethyl)carbamoyl]oxy}methyl) phenyl acetate 2-methoxy-4-({[(2-phenylethyl)carbamoyl]oxy}methyl) phenyl acetate 4-({[(cyclohexylmethyl)carbamoyl]oxy}methyl)-2-methoxyphenyl acetate
4-{[(2,3-dihydro-1H-inden-2-yl carbamoyl)oxy]methyl}-2-methoxyphenyl acetate
4-({[(3,3-dimethylbutyl)carbamoyl]oxy}methyl)-2-methoxyphenyl acetate
2-methoxy-4-[({[2-(morpholin-4-yl)ethyl]carbamoyl}oxy)methyl]phenyl acetate
4-{[(ethylcarbamoyl)oxy]methyl}-2-methoxyphenyl acetate
ethyl[({[4-(acetyloxy)-3-methoxybenzyl]oxy}carbonyl)amino]acetate
ethyl 2[({[4-(acetoxy)-3-methoxybenzyl]oxy}carbonyl)amino]-3-methylbutanoate The compounds of the invention are prepared by one or more of the synthetic routes described below.

Preparation of the Carbamates

Three synthetic pathways, A, B, and C, were employed commencing with 3-methoxy-4-hydroxybenzyl alcohol (commonly known as vanillyl alcohol). It is necessary to first acylate the phenolic hydroxyl to direct the subsequent condensation—especially in Pathway C—onto the benzyl alcohol. This acyl protected phenol provides essential stability to the thiazolide-activated intermediate (VII in Scheme 2) and it also generates the final carbamates (V in Scheme 2) as ester pro-drugs which release the vanilloid ring by in situ hydrolysis. In summary, unless the phenolic hydroxyl is acylated to produce (I), the p-hydroxybenzyloxy moiety proved to be point of instability in the carbamate products.

The 3-methoxy-4-acetoxybenzyl alcohol (I) was reacted with either a suitable isocyanate (II) (Method A, Isocyanate Pathway), or with a suitable aliphatic amine (IV) (Method B, Carbonyldiimidazole Pathway), or with the N-chloroformylthiazolide (VI) (Method C, Thiazolidine Pathway). A general description of each method follows with specific examples of carbamates prepared by each route.

General Experimental Procedures
Synthesis

Anhydrous tetrahydrofuran (THF) and anhydrous dichloromethane ($CH_2Cl_2$) were purchased from Alfa Aesar. HPLC grade $CH_2Cl_2$ was obtained from EM Science. Triethylamine and Hünig's base were supplied by Sigma-Aldrich, and mercaptothiazolide (MTA or thiazolidine-2-thione) and vanillyl alcohol were purchased from Alfa Aesar. Silica gel 60, 230-400 mesh, was obtained from either Alfa Aesar or Sorbent Technologies. Solvents for column chromatography included hexanes (Fisher Scientific and EM Science), ethyl acetate, dichloromethane and methanol (EM Science), and acetone (Fisher Scientific). All other commercially available reagents were from Sigma-Aldrich, Alfa Aesar or Acros Organics. All NMR solvents were purchased from Cambridge Isotope Laboratories, Inc. NMR spectra were recorded on a Bruker 500 MHz instrument. Melting points were recorded on a Mel-Temp instrument and are uncorrected. Mass spectral data were obtained from the Mass Spectrometry Facility, Department of Chemistry and Biochemistry, University of Notre Dame.

Preparation of Carbamates:
General Method [A]: The Isocyanate Pathway

The benzyl alcohol I (1 eq) and $NEt_3$ (1.5 eq) were dissolved in anhydrous $CH_2Cl_2$ (4 mL/eq of alcohol I), and the resulting solution was stirred at room temperature. To the solution was added the isocyanate (1 eq). The progress of the reaction was monitored by thin layer chromatography (TLC). Typically, after the reaction mixture was stirred overnight a second equivalent of isocyanate was added. Once TLC analysis indicated completion of reaction, the reaction mixture was diluted with $CH_2Cl_2$, and the resulting solution was extracted with 1N aqueous HCl and saturated aqueous NaCl. The organic layer was dried over anhydrous $MgSO_4$, filtered and concentrated. The crude material was purified by column chromatography on silica gel to yield the target carbamates.

General Method [B]: The Carbonyldiimidazole (CDI) Pathway

To a solution at room temperature of requisite benzyl alcohol I (1 eq) in anhydrous $CH_2Cl_2$ (5 mL/eq of alcohol I) was added CDI (1.1 eq). After the reaction solution was stirred for six hours a small drop of water was added, and the mixture was stirred vigorously for five minutes, after which time the requisite amine (IV) (1.1 eq) was added. The progress of the reaction was monitored by TLC. Upon completion of reaction, the mixture was diluted with $CH_2Cl_2$, and the solution washed with aqueous 1N HCl, water, and saturated aqueous NaCl. The organic layer was dried over anhydrous $MgSO_4$, filtered and concentrated. The crude product (V) was purified by column chromatography on silica gel.

General Method [C]: The Thiazolidine Pathway
Utility of the Thiazolidine Pathway As a synthetic construct, carbamates can be envisioned as an alcohol and an amine linked by a carbonyl moiety which has been previously activated for dual displacement. In other words Alcohol part-CO-Amine part can be assembled from Leaving group-CO-Leaving group by successive displacement of the Leaving Groups by an alcohol and an amine in appropriate sequence. For this purpose mercaptothiazolidine-promoted coupling (Nagao 1980) with the specific application of N-chloroformylthiazolidine-2-thione (VI) (see Scheme 1 below), offers a unique set of circumstances to the synthetic chemist. Our process for the synthesis of VI uses diphosgene—a much safer chloroformylating agent than phosgene—and permits nearly quantitative yields by use of an easily-remove heterogeneous base catalyst, poly(4-vinylpyridine). This route—which prepares and uses the N-chloroformyl VI in situ—provides visual monitoring of completion (yellow to colorless transition), high reactivity, selectivity, extraordinary stability of the benzyloxycarbonyl intermediates (viz., VII), suitability for use in parallel syntheses and combichem, recoverability of the MTA, and reaction compatibility with alcohols, water, and other polar solvents. Of all the common "activated" carbonyl species traditionally employed in syntheses of carbamates, such as aryl or alkyl chloroformates, isocyanates, or carbonylimidazoles, it is the 3-benzyloxycarbonylthiazolidine-2-thiones (VII in Scheme 1) which are most useful in multi-product parallel syntheses. These adducts are stable solids with shelf lives>three years. They are not decomposed by exposures to moisture or oxygen. They are easily weighed and charged to reaction flasks. Their condensation with amines—to yield carbamates—often requires neither heat and nor lengthy reaction time.

Scheme 1. Mercaptothiazoline (MTA)-Promoted Carbamate Synthesis

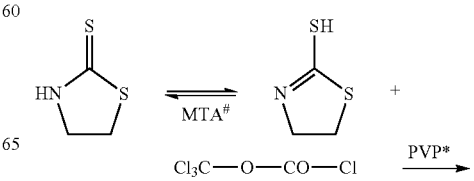

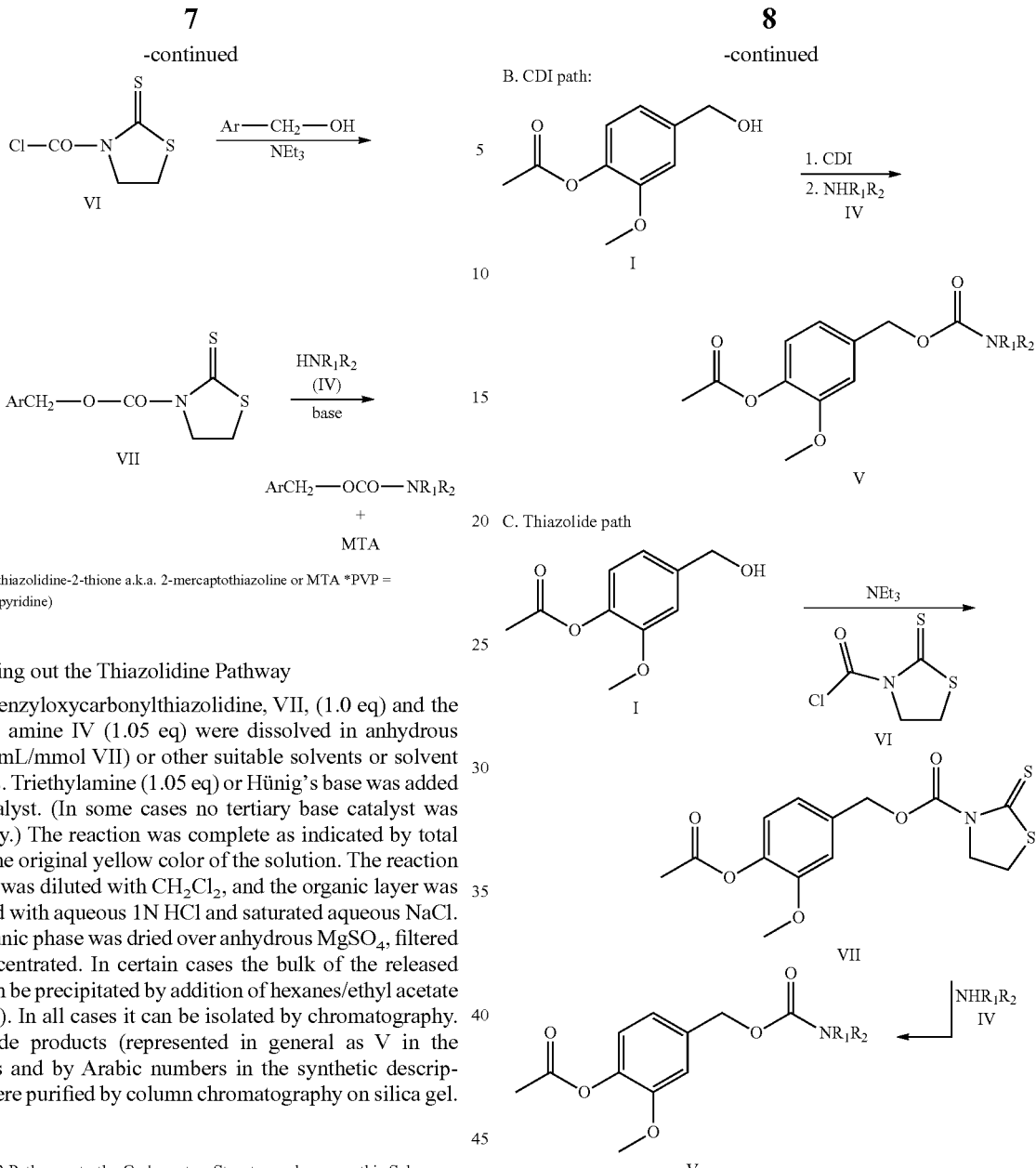

tautomeric thiazolidine-2-thione a.k.a. 2-mercaptothiazoline or MTA *PVP = poly(4-vinylpyridine)

Carrying out the Thiazolidine Pathway

The benzyloxycarbonylthiazolidine, VII, (1.0 eq) and the requisite amine IV (1.05 eq) were dissolved in anhydrous THF (5 mL/mmol VII) or other suitable solvents or solvent mixtures. Triethylamine (1.05 eq) or Hünig's base was added as a catalyst. (In some cases no tertiary base catalyst was necessary.) The reaction was complete as indicated by total loss of the original yellow color of the solution. The reaction solution was diluted with $CH_2Cl_2$, and the organic layer was extracted with aqueous 1N HCl and saturated aqueous NaCl. The organic phase was dried over anhydrous $MgSO_4$, filtered and concentrated. In certain cases the bulk of the released MTA can be precipitated by addition of hexanes/ethyl acetate (7:3, v/v). In all cases it can be isolated by chromatography. The crude products (represented in general as V in the Schemes and by Arabic numbers in the synthetic descriptions) were purified by column chromatography on silica gel.

Scheme 2 Pathways to the Carbamates. Structures shown on this Scheme bear Roman numerals. Compounds in the Experimental Section have Arabic numbers.

A. Isocyanate path:

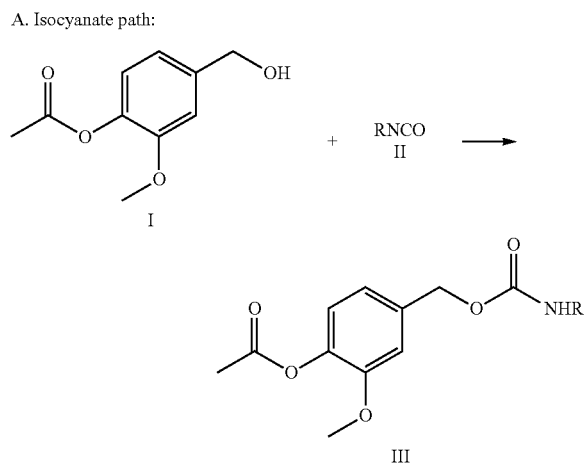

Compounds of the present invention act as inhibitors of FAAH and have utility as therapeutics for disease states in which the regulation of FAAH is desired. Such disease states include but are not limited to Alzheimer's dementia, Parkinson's disease, depression, pain, rheumatoid arthritis, pathophysiology of mood disorders, multiple sclerosis, and inflammation.

In addition, compounds of this invention also act as antagonists of the TRPV1 receptor and regulators of calcium flux and hence are useful as therapeutics for disease states in which TRPV1 antagonism and calcium flux regulation are desired and wherein such disease states include but are not limited to Huntington's disease, hypertension, arthritis, allergic airway inflammation, Crohn's disease, ulcerative colitis, and neuropathic pain.

FAAH Inhibition

It is well recognized that the endocannabinoid system is a key lipid signaling pathway that has been implicated in many physiological processes including pain control, fat metabolism, neurological diseases and inflammation. Key endocannabinoids released from lipid precursors in this pathway include 2-arachidonoylglycerol and arachidonoylethanolamide. These signaling molecules are known to mediate their action in peripheral tissues, at least in part, by binding to the cannabinoid receptors CB1 and CB2. An enzyme known to be important in degrading endocannabinoid mediators including arachidonoylethanolamide and related fatty acid amides is the serine protease FAAH. Inhibitors of this enzyme prevent degradation of endocannabinoids and other fatty acid amides; where increased levels of these mediators may be beneficial, these inhibitors are likely to be of therapeutic value.

The candidate therapeutics were assayed as inhibitors of FAAH using an FAAH Inhibitor Screening Assay Kit from Cayman Chemical (Ann Arbor, Mich.). This kit provides a fluorescence-based method for screening FAAH inhibitors. In this assay, human recombinant FAAH hydrolyzes 7-amino-4-methylcoumarin (AMC)-arachidonoyl amide resulting in the release of the fluorescent product AMC. In our studies, AMC was quantified on a Molecular Devices M5 microplate reader using an excitation wavelength of 340 nm and an emission wavelength of 450 nm, Reactions in 0.2 ml were run as directed by the manufacturer for 30 min at 37° C. using 96 well plates with each well containing FAAH in 125 mM Tris-HCl buffer, pH 9.0 containing 1 mM EDTA and 20 micromolar (final concentration) of the substrate 7-amino-4-methylcoumarin (AMC)-arachidonoyl amide in the absence and presence of increasing concentrations of our candidate therapeutics. Data is presented as the concentration of candidate therapeutic inhibiting FAAH activity by 50% ($IC_{50}$). Representative $IC_{50}$ values are included on Tablet.

Although it is apparent that electronic factors and steric bulk at or near the carbamate's hydrolysis site can reduce the activity in the FAAH assay (e.g., Compound 7 with N,N-dibutyl and Compound 14 with 2-indanyl), the most obvious correlation with $IC_{50}$ is the molecule's relative lipophilicity or cLogP. cLogP's were determined by the VG Method and for the water-soluble carbamates such as 17, 18, and 19 are respectively 0.50, 1.1, and 0.78. These compounds were either modestly potent or showed only weak inhibition at the highest dose tested. Compound 2, the n-butyl carbamate with a cLogP of 2.07, was the least active of all the common alkyl amine carbamates tested while Compound 10, the dodecyl derivative was not only the most effective ($IC_{50}$ 8 micromolar) but also the most lipophilic, cLogP=5.24. In this series, fatty acid amide hydrolase does require a lipophilic inhibitor. The VG Method is available at (http://intro.bio.umb.edu/111-112/OLLM/111F98/newclogp.html).

Functional Assay for Antagonists of TRPV1 Receptors.

The ability of vanilloid carbamates to inhibit capsaicin-induced calcium mobilization in HEK293 cells stably expressing high affinity TRP-V1 receptors was assayed as described in the literature (Swanson et al. 2005) except that a Molecular Devices M5 spectrofluorometer was used to monitor changes in levels of intracellular calcium. Briefly, HEK293-TRPV1 cells were preloaded for 30 minutes in 10 micromolar medium of the intracellular fluorescent calcium indicator Fluo-4 (Molecular Probes). After 30 minutes, 0.8 ml of cells ($2\times10^6$/ml) were placed in a fluorometer cuvette. To activate the TRPV1 receptors on the cells, capsaicin was added to achieve 10 micromolar concentration in the cuvette to stimulate intracellular calcium mobilization (De Petrocellis et al. 2009). Changes in Fluo-4 fluorescence were then recorded (excitation=488 nm; emission=516 nm). Under these conditions, capsaicin readily induces increases in intracellular calcium (Swanson et al. 2005). To test vanilloid cabamates as antagonists of the TRPV1 receptor, cells were pretreated at 100 micromolar concentrations of the respective compounds in the cuvettes for 15 minutes prior to the addition of capsaicin. After an additional 30 minutes, the percent inhibition of capsaicin-induced calcium mobilization was recorded.

Results of this assay for some of the compounds of this invention are presented in Table 1.

TABLE 1

| Compound No | FAAH (µM, IC50) |
|---|---|
| 1 | 104 |
| 2 | 338 |
| 3 | 333 |
| 4 | 88 |
| 5 | 62 |
| 6 | 67 |
| 7 | 135 |
| 8 | 28 |
| 9 | 31 |
| 10 | 8 |
| 11 | 21 |
| 12 | 8 |
| 13 | 85 |
| 14 | 100 |
| 16 | 25 |
| 17 | 410 |
| 18 | >900 |
| 19 | >900 |
| 20 | 749 |

In Vivo Inflammation Suppressant Measurements: Procedure to Assess Anti-Inflammatory Activity Using the Mouse Ear Inflammation Assay The mouse ear inflammation (or edema or vesicant) model (MEVM) was employed to assess the anti-inflammatory activity of the carbamates. This edema assay has been used historically to screen for inhibitors of inflammation (Casillas et al., 1997; Casillas et al., 2000 Huang et al., 1988, 1994). In this technique, an irritant is applied topically to the mouse ear; after an appropriate period of time, the irritant induces edema and increases the weight of the ear, a hallmark of the inflammatory process. Anti-inflammatory agents can effectively suppress irritant-induced increases in ear weight.

Using TPA to Induce Inflammation:

To demonstrate the efficacy of our compounds, we used the inflammation-inducing agent TPA (also known as phorbol ester or 12-O-tetradecanoylphorbol-13-acetate. In our assay, mice (female CD-1 mice, 4-5 weeks of age, 6-10 animals/group) were treated on the inner surface of the right ear with 20 microliters of methylene chloride (control) or TPA (1.5 micromoles dissolved in 20 microliters of methylene chloride per application). Test compounds (1-2 micromoles) were applied to the ears 10 minutes prior to treatment with control or TPA as the inflammatory agent. After 6 hours, animals were sacrificed and ear punches (6 mm diameter) were taken and weighed. Anti-inflammatory activities of our candidate therapeutics were determined by the relative percent inhibition of the edema induced by TPA as shown in Table 2 wherein compounds which actively suppressed the edema by >80% were scored (* * * * *), >70% were scored (* * * *), those >60% are marked (* * *), those >50% are (* *), and those from 5% to 50% suppression are coded (*).

TABLE 2

| Compound No. | Rel. TPA Inflammatory Suppression |
|---|---|
| 2 | *** |
| 3 | ** |
| 4 | * |
| 5 | * |
| 6 | ** |
| 7 | ** |
| 8 | ** |
| 9 | **** |
| 10 | **** |
| 11 | ***** |
| 12 | ***** |
| 13 | ** |
| 14 | **** |
| 15 | * |
| 16 | *** |
| 17 | * |
| 18 | * |
| 19 | *** |
| Diclofenac | 35% |
| (S)-Naproxen | 42% |

Using Chloroethyl Ethyl Sulfide (CEES) to Induce Inflammation

2-Chloroethyl ethyl sulfide (CEES) is a potent skin vesicant and inflammatory agent structurally related to sulfur mustard. Sulfur mustards have previously been used to screen for anti-inflammatory agents using the mouse ear model (Casillas et al., 1997; Casillas et al., 2000). In our assay, mice (female CD-1 mice, 4-5 weeks of age, 6-10 animals/group) were treated on the inner surface of the right ear with 20 microliters of methylene chloride (control) or CEES (2.5 mg/ml) in methylene chloride. Test compounds (1-2 micromoles) were applied to the ears 10 minutes prior to treatment with control or with CEES as the vesicant-inflammatory agent. After 6 hours, animals were sacrificed and ear punches (6 mm diameter) were taken and weighed. Anti-inflammatory activities of our candidate therapeutics were determined by the percent inhibition of the edema induced by CEES.

In response to the CEES-inflamed ears Compound 12 provided a 56% suppression and Compound 11 provided a 51% suppression.

Dosage Formulation

The drugs reported herein can be administered in effective amounts for the clinical condition for which the substance is indicated by either oral, ophthalmic, or topical formulation. The concentration of the pharmaceutical in its formulated form can be established by one skilled in the art and will vary with the nature and severity of the dysfunction as well as the pharmacokinetics/pharmacodynamics and in vivo release of the substance.

The oral solid dosage—troches, capsules, or pills—normally contains excipients which provide dilution, extended release, and processing facility. Starch, alkylated celluloses, talc, lactose, silicon dioxide, and magnesium stearate are but a few of the performance enhancing additives. The principles for selection of the best excipient(s) for a given API are well documented and easily applied by one skilled in the arts. (R. K. Verma et al. 2005).

Liquid oral dosage forms may also prove utilitarian. The active ingredient dissolved in a fatty oil in sealed capsules can provide a suitable gastric or enteric release. A syrup, elixir, or a suspension can also provide oral bioavailability.

Topical or ophthalmic formulations can include sterile water or saline, polyethylene glycols, biocompatible oils, glycerine, or other suitable solvents with or without emulsifiers.

Preservatives such as antioxidants, antibacterials, buffers, chelating agents, and tonicity modifiers (low molecular weight saccharides and sodium chloride) can also be included. While concentrations vary widely, the typical concentration of the active ingredient in the lipid, oil, cream, or lotion topical formulation is 1-4%. Transdermal dosage forms are a special variant of topicals which contain penetration enhancers, skin softeners, and viscosity modulators blended with the pharmaceutically active substance on an impermeable backing with an edge-coated adhesive.

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric, 2-naphthalenesulfonic and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

The following examples will further illustrate this invention but are not intended to limit it in anyway. In Table 3, typical compounds of the present invention are listed. Following Table 3, representative illustrative preparations of compounds of the invention are described.

TABLE 3

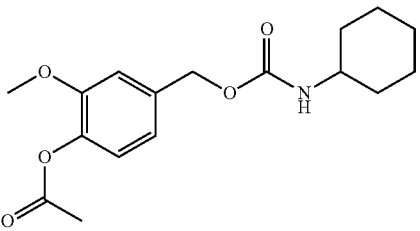

| Compound No. | R* | $R_1$ | $R_2$ | Method of synthesis |
|---|---|---|---|---|
| 1 | $CH_3$ | H | cyclohexyl | A, C |
| 2 | $CH_3$ | H | n-butyl | A |
| 3 | $CH_3$ | H | n-hexyl | A |
| 4 | $CH_3$ | H | n-octyl | A |
| 5 | $CH_3$ | H | n-decyl | B |
| 6 | $CH_3$ | H | n-heptyl | C |
| 7 | $CH_3$ | n-butyl | n-butyl | C |
| 8 | $CH_3$ | H | benzyl | C |
| 9 | $CH_3$ | H | 2-ethylhexyl | C |
| 10 | $CH_3$ | H | n-dodecyl | C |
| 11 | $CH_3$ | H | 2-phenoxy ethyl | C |
| 12 | $CH_3$ | H | phenethyl | C |
| 13 | $CH_3$ | H | cyclohexylmethyl | C |
| 14 | $CH_3$ | H | 2-indanyl | C |
| 15 | $CH_3$ | H | 2-methoxyethyl | B |
| 16 | $CH_3$ | H | 3,3-dimethylbutyl | C |
| 17 | $CH_3$ | H | 2-(4-morpholino)ethyl | C |
| 18 | $CH_3$ | H | ethyl | C |
| 19 | $CH_3$ | H | ethyl-2-glycinyl | C |
| 20 | $CH_3$ | H | ethly-2-valinyl | C |

EXAMPLE 1

4-(hydroxymethyl)-2-methoxyphenyl acetate (I)

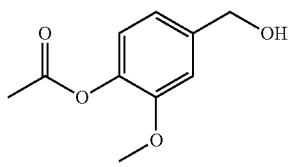

A partial solution of 4-hydroxy-3-methoxybenzyl alcohol (1.23 g, 8 mmol), triethylamine (810 mg, 1.12 mL, 8 mmol) and 32 mL of dry $CH_2Cl_2$ was chilled in an ice bath. To the cold mixture was added dropwise acetyl chloride (628 mg, 570 μL, 8 mmol). The mixture was stirred at ice bath temperature 1 for one hour. Stirring at room temperature was allowed to take place overnight. The reaction mixture was diluted with $CH_2Cl_2$ and extracted with 1N HCl, water and saturated NaCl. The organic layer was dried over $MgSO_4$, filtered and concentrated. Column chromatography on silica gel using $CH_2Cl_2$/MeOH (98:2, v/v) gave 548 mg (35%) of CO as a clear oil: $R_f$=0.22 (hexanes/ethyl acetate, 6:4 v/v); $^1$HNMR (CDCl$_3$) δ 7.00 (d, $^4J$=1.5 Hz, 1H), 6.99 (d, $^3J$=8.5 Hz, 1H), 6.89 (dd, $^3J$=8.0 Hz, $^4J$=1.5 Hz, 1H), 5.27 (s, 2H), 4.66 (s, 2H), 3.83 (s, 3H) and 2.30 (s, 3H). Exact mass (FAB$^+$) calculated for $C_{10}H_{12}O_4$[M$^+$] 196.0736. found 196.0739.

4-{[(cyclohexylcarbamoyl)oxy]methyl}-2-methoxyphenyl acetate (1)

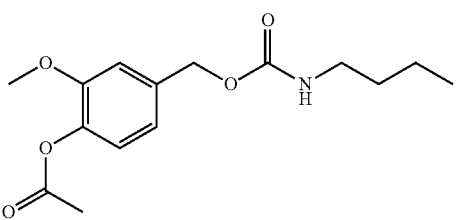

Compound I (88 mg, 0.448 mmol) was dissolved in 2 mL of dry $CH_2Cl_2$. To the stirred solution was added cyclohexylisocyanate (56 mg, 57 μl, 0.448 mmol), and three hours later 0.2 eq of NEt$_3$ was added. After stirring overnight, and addition 1 equivalent of isocyanate and 1.28 equivalents of NEt$_3$ were added. The reaction mixture was allowed to stir for two more days at which time TLC indicated that the reaction was fairly complete. The reaction mixture was diluted with $CH_2Cl_2$ and extracted with 1N HCl and saturated NaCl. The organic layer was dried over $MgSO_4$, filtered and concentrated. Column chromatography on silica gel using $CH_2Cl_2$/acetone (97:3, v/v) gave 107 mg (74%) of a white solid: mp=98-100° C. (uncorrected); $R_f$=0.27 (dichloromethane/acetone, 97:3, v/v), $^1$HNMR (CDCl$_3$) δ 6.99 (d, $^3J$=8.0 Hz, 1H), 6.95 (d, $^4J$=1.5 Hz, 1H), 6.92 (dd, $^3J$=8.0 Hz, $^4J$=2.0 Hz, 1H), 5.03 (s, 2H), 4.61 (bs, 1H, NH), 3.82 (s, 3H), 3.48 (bs, 1H), 2.29 (s, 3H), 1.93-1.91 (m, 2H), 1.70 (m, 2H), 1.60-1.56 (m, 1H), 1.37-1.29 (m, 2H) and 1.18-1.08 (m, 3H). Exact mass (FAB$^+$) calculated for $C_{17}H_{24}NO_5$ [M$^+$] 321.1576. found 321.1562.

EXAMPLE 2

4-{[(butylcarbamoyl)oxy]methyl}-2-methoxyphenyl acetate (2)

To a solution of compound I (121 mg, 0.619 mmol) and NEt$_3$ (94 mg, 129 μL, 1.5 eq) in 3 mL of dry $CH_2Cl_2$ was added n-butylisocyanate (123 mg, 139 μL, 2 eq), and the solution was stirred at room temperature for three days, at which time 0.5 eq of isocyanate was added. After three days, the TLC indicated completion of reaction. The reaction mixture was worked up according to the preparation of 2, vide supra, and purified by column chromatography on silca gel while eluting with CH$_2$Cl$_2$/acetone (97:3, v/v) to give 181 mg (99%) of a clear oil: R$_f$=0.52 (dichloromethane/acetone, 97:3, v/v); $^1$HNMR (CDCl$_3$) δ 6.99 (d, $^3$J=8.0 Hz, 1H), 6.95 (bs, 1H), 6.92 (bd, $^3$J=8.0 Hz, 1H), 5.04 (s, 2H), 4.69 (bs 1H, NH), 3.82 (s, 3H), 3.18 (m, 2H), 2.29 (s, 3H), 1.47 (m, 2H), 1.33 (m, 2H) and 0.90 (t, $^3$J=7.3 Hz, 3H). Exact mass (FAB$^+$) calculated for C$_{15}$H$_{21}$NO$_5$ [M$^+$] 295.1420. found 295.1441.

EXAMPLE 3

4-{[(hexylcarbamoyl)oxy]methyl}-2-methoxyphenyl acetate (3)

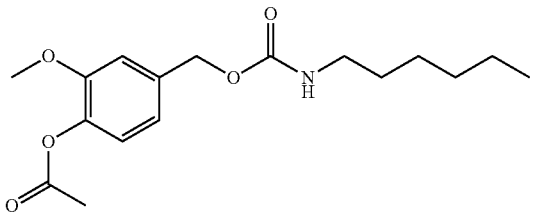 [SMILES: CCCCCCNC(=O)OCc1ccc(OC(C)=O)c(OC)c1]

To a solution of compound I (110 mg, 0.562 mmol) and NEt$_3$ (85 mg, 118 μL, 1.5 eq) in 2.5 mL of dry CH$_2$Cl$_2$ was added n-hexylisocyanate (72 mg, 82 μL, 1 eq), and the solution was stirred at room temperature for one day, at which time 1 eq of isocyante was added. After stirring for an additional five days, the reaction mixture was worked up according to the preparation of 2. Column chromatography on silica gel eluting with CH$_2$Cl$_2$/acetone (97:3, v/v) gave 160 mg (88%) of a clear oil: R$_f$=0.56 (dichloromethane/acetone, 97:3, v/v); $^1$HNMR (CDCl$_3$) δ 6.98 (d, $^3$J=8.0 Hz, 1H), 6.95 (d, $^4$J=1.65 Hz, 1H), 6.91 (dd, $^3$J=8.0 Hz, $^4$J=1.7 Hz 1H), 5.04 (s, 2H), 4.71 (bs 1H, NH), 3.81 (s, 3H), 3.24-3.15 (m, 2H), 2.29 (s, 3H), 1.53-1.44 (m, 2H), 1.32-1.21 (m, 6H) and 0.87-0.84 (m, 3H). Exact mass (FAB$^+$) calculated for C$_{17}$H$_{26}$NO$_5$ [M$^+$] 323.1732. found 323.1745.

EXAMPLE 4

4-{[(octylcarbamoyl)oxy]methyl}-2-methoxyphenyl acetate (4)

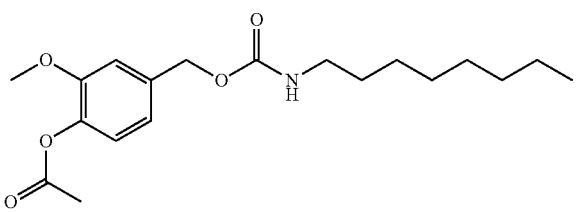 [SMILES: CCCCCCCCNC(=O)OCc1ccc(OC(C)=O)c(OC)c1]

n-Octylisocyanate (84 mg, 95 μL, 0.535 mmol) was added to a solution of I (105 mg, 0.535 mmol) and NEt$_3$ (81 mg, 112 μL, 1.5 eq) in 2.4 mL of dry CH$_2$Cl$_2$, and the solution was stirred at room temperature overnight. One equivalent of isocyanate was then added, and stirring continued for two days. After work up as described for 2, column chromatography on silica gel using CH$_2$Cl$_2$/acetone (97:3, v/v) provided 143 mg (76%) of a white solid: mp=48-49° C. (uncorrected); R$_f$=0.56 (dichloromethane/acetone, 97:3, v/v); $^1$HNMR (CDCl$_3$) δ 6.99 (d, $^3$J=8.0 Hz, 1H), 6.95 (d, $^4$J=1.6 Hz, 1H), 6.93 (dd, $^3$J=8.0 Hz, $^4$J=1.8 Hz, 1H), 5.04 (s, 2H), 4.69 (bs 1H, NH), 3.82 (s, 3H), 3.17 (m, 2H), 2.29 (s, 3H), 1.50-1.45 (m, 2H), 1.31-1.20 (m, 10H) and 0.86 ((t, $^3$J=7 Hz, 3H). Exact mass (FAB$^+$) calculated for C$_{19}$H$_{30}$NO$_5$ [M+H] 352.2118. found 352.2136.

EXAMPLE 5

4-{[(decylcarbamoyl)oxy]methyl}-2-methoxyphenyl acetate (5)

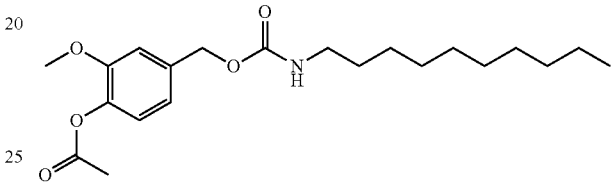

Compound I (216.5 mg, 1.104 mmol) was dissolved in dry dichloromethane (5.5 mL, 5 mL/mmol I). The solution was placed under a positive N$_2$ pressure, and carbonyldiimidazole (CDI) (197 mg, 1.1×1.104 mmol) was added in one portion. The reaction solution was stirred 6 hours at room temperature. One drop of water was then added, and the mixture was stirred for five minutes. Decylamine (191 mg, 243 μL, 1.1× 1.104 mmol) was added, and the solution was stirred overnight. The reaction solution was diluted with dichloromethane and extracted with 1N HCl, water and saturated NaCl. The organic layer was dried over MgSO$_4$, filtered and concentrated. Purification was achieved by column chromatography on silica gel using dichloromethane/acetone (97:3, v/v) as eluant to give 131 mg (31%) of a white solid: mp=55-57° C. (uncorrected); R$_f$=0.61 (dichloromethane/acetone, 97:3, v/v); $^1$HNMR (CDCl$_3$) δ 6.99 (d, $^3$J=8.0 Hz, 1H), 6.95 (d, $^4$J=1.45 Hz, 1H), 6.92 (bd, $^3$J=8.0 Hz, 1H), 5.04 (s, 2H), 4.69 (bs, 1H, NH), 3.82 (s, 3H), 3.17 (apparent quartet, $^3$J=6.7 Hz, 2H), 2.29 (s, 3H), 1.52-1.44 (m, 2H), 1.32-1.18 (m, 14H) and 0.86 (t, $^3$J=7 Hz, 3H). Exact mass (FAB$^+$) calculated for C$_{21}$H$_{33}$NO$_5$ [M$^+$] 379.2358. found 379.2357.

EXAMPLE 6

2-methoxy-4-({[(2-methoxyethyl)carbamoyl]oxy}methyl)phenyl acetate (15)

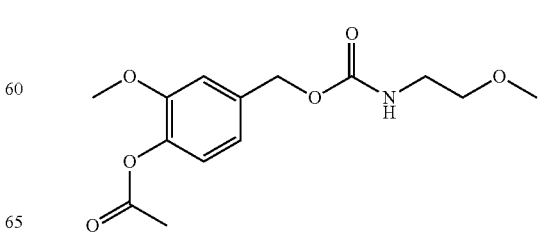

To a solution of I (788.6 mg, 4.02 mmol) in anhydrous CH$_2$Cl$_2$ (15 mL) was added CDI (815 mg, 1.25×4.02 mmol). The resulting solution was stirred at room temperature for 4 hours. The solution was diluted with CH$_2$Cl$_2$ and washed with 2×20 mL of water. The organic layer was concentrated, the residue dissolved in CH$_2$Cl$_2$ (15 mL), and finally 2-methoxyethylamine (302 mg, 346 µL, 4.02 mmol) was added. The reaction solution was stirred at room temperature for 1 hour. The mixture was diluted with CH$_2$Cl$_2$, washed with 1N HCl, water and saturated NaCl. The organic layer was dried over anhydrous MgSO$_4$, filtered and concentrated. Purification was achieved by column chromatography on silica gel using dichloromethane/methanol (97:3, v/v) as eluant to render 80.2 mg (7%) of 15 as a clear yellow oil: $R_f$=0.55 (CH$_2$Cl$_2$/MeOH, 97:3, v/v), $R_f$=0.18 (hexanes/ethyl acetate, 1:1, v/v); $^1$HNMR (CDCl$_3$) δ 6.98 (d, $^3$J=8.0 Hz, 1H), 6.95 (d, $^4$J=1.65 Hz, 1H), 6.92 (dd, $^3$J=8.0 Hz, $^4$J=1.70 Hz, 1H), 5.28 (s, 1H, NH), 5.05 (s, 2H), 3.80 (s, 3H), 3.44 (t, $^3$J=5.0 Hz, 2H), 3.36 (q, $^3$J=5.2 Hz, 2H, NCH$_2$), 3.33 (s, 3H) and 2.29 (s, 3H). Although TLC results showed that the reaction was essentially complete, the affinity of 15 for the column and its partial instability under chromatographic conditions, decreased the isolated yield.

EXAMPLE 7

4-(acetyloxy)-3-methoxybenzyl 2-thioxo-1,3-thiazolidine-3-carboxylate (VII)

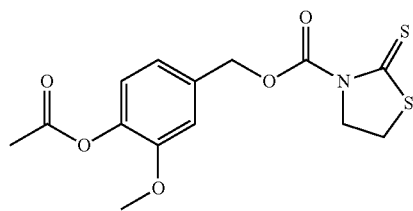 [SMILES: COc1cc(COC(=O)N2CCSC2=S)ccc1OC(C)=O]

To a flask purged with N$_2$ was added 2-mercaptothiazoline (MTA) (167 mg, 1.1×1.27 mmol) and polyvinyl pyridine (PVP) (159 mg, 8.8 mg/eq, 1.1×1.27 mmol) (see Scheme 1). Seven mL of dry CH$_2$Cl$_2$ (5 mL/mmol MTA) were added to the flask while maintaining a positive N$_2$ pressure. The suspension was stirred at room temperature, and diphosgene (137 mg, 85 µL, 0.55×1.27 mmol) was added dropwise. After being stirred for five hours the intermediate chloroformylthiazolidine (VI) was filtered through a sintered glass filter into a flask containing the benzyl alcohol, I, (250 mg, 1.27 mmol) dissolved in 1-2 mL of dry CH$_2$Cl$_2$. The beads of PVP thus removed were rinsed in portions with a total of 5 mL of fresh, dry CH$_2$Cl$_2$. The flask containing the filtrate was placed under a positive N$_2$ pressure and immersed in an ice bath. To the cooled solution was added NEt$_3$ (141 mg, 195 µL, 1.1×1.27 mmol) directly into the stirred solution, via syringe. After stirring overnight the diluted reaction solution was extracted with 1N HCl, water and saturated NaCl. The organic layer was dried over MgSO$_4$, filtered and concentrated. The crude product was purified twice by column chromatography on silica gel eluting with dichloromethane/methanol (98:2, v/v) to give 160 mg (37%) of VII as a nearly pure yellow solid (compound appears to decompose slightly while on the column); $R_f$=0.62 (dichloromethane/methanol, 98:2, v/v); $^1$HNMR (CDCl$_3$) δ 7.11 (d, $^4$J=1.65 Hz, 1H), 7.01-6.99 (m, 1H), 6.98-6.95 (m, 1H), 5.27 (s, 2H), 4.52 (t, $^3$J=7.5 Hz), 3.82 (s, 3H), 3.29 (t, $^3$J=7.5 Hz, 2H) and 2.30 (s, 3H). Exact mass (ESI) calculated for C$_{14}$H$_{15}$NNaO$_5$S$_2$ [M+Na] 364.0284. found 364.0277.

4-{[(heptylcarbamoyl)oxy]methyl}-2-methoxyphenyl acetate (6)

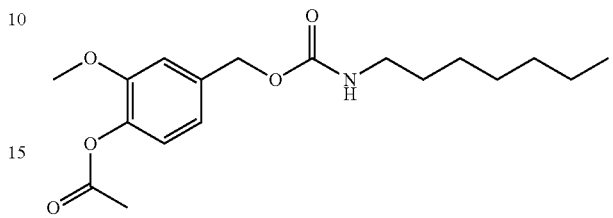

A yellow solution of VII (87 mg, 0.255 mmol), n-heptylamine (31 mg, 1.05×0.255 mmol) and triethylamine (26 mg, 36 µL, 0.255 mmol) in 3 mL of dichloromethane was stirred at room temperature overnight. The reaction was worked up as described for 7. The product was purified by preparative thick layer chromatography using dichloromethane/diisopropyl ether, 9:1, v/v, as the developing solvent. The result was 58 mg (67%) of 6 as a clear oil: $R_f$=0.53 (dichloromethane/acetone, 97:3, v/v); $^1$HNMR (CDCl$_3$) δ 6.98 (d, $^3$J=8.0 Hz, 1H), 6.94 (s, 1H), 6.91 (d, $^3$J=8.0 Hz, 1H), 4.98 (s, 2H), 4.73 (bs 1H, NH), 3.81 (s, 3H), 3.18-3.14 (m, 2H), 2.29 (s, 3H), 1.50-1.43 (m, 2H), 1.31-1.19 (m, 8H) and 0.85 (t, $^3$J=7.0 Hz, 3H). Exact mass (FAB$^+$) calculated for C$_{18}$H$_{27}$NO$_5$ [M$^+$] 337.1889. found 337.1895.

EXAMPLE 8

4-{[(dibutylcarbamoyl)oxy]methyl}-2-methoxyphenyl acetate (7)

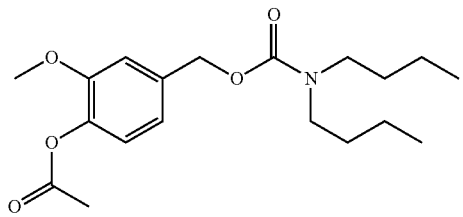 [SMILES: CCCCN(CCCC)C(=O)OCc1ccc(OC(C)=O)c(OC)c1]

A yellow solution of VII (159.9 mg, 0.468 mmol), di-n-butylamine (64 mg, 83 µL, 1.05×0.468 mmol) and triethylamine (47 mg, 65 µL, 0.468 mmol) in 2.5 mL of dry THF was stirred at room temperature overnight. One equivalent of diisopropylethylamine and 0.5 equivalent of dibutylamine were added, and stirring continued for three days. The solution was diluted with dichloromethane and extracted with 1N HCl and then saturated NaCl. The organic layer was dried over MgSO$_4$, filtered and concentrated. The crude material was covered with 5 mL of 7:3 hexanes/ethyl acetate solution and a few drops of ethyl acetate to render a solution. Upon standing overnight, much of the mercaptothiazoline crystallized out. The supernatant was withdrawn, and the crystals were rinsed with a small portion of 7:3 hexanes/ethyl acetate. The combined organic layer was concentrated and redissolved in dichloromethane/diisopropyl ether (86:14, v/v).

Column chromatography on silica gel eluting with dichloromethane/diisopropyl ether (86:14, v/v) gave 113.9 mg (69%) of 7 as a clear oil: $R_f$=0.72 (dichloromethane/diisopropyl ether, 86:14, v/v); $^1$HNMR (CDCl$_3$) δ 6.98 (d, $^3$J=8.0 Hz, 1H), 6.95 (d, $^4$J=1.65 Hz, 1H), 6.90 (dd, $^3$J=8.0 Hz, $^4$J=1.75 Hz, 1H), 5.07 (s, 2H), 3.80 (s, 3H), 3.24-3.18 (m, 4H), 2.29 (s, 3H), 1.53-1.43 (m, 4H), 1.32-1.21 (m, 4H) and 0.92-0.85 (m, 6H). Exact mass (FAB$^+$) calculated for C$_{19}$H$_{30}$NO$_5$ [M+H] 352.2118. found 352.2115.

EXAMPLE 9

4-{[(benzylcarbamoyl)oxy]methyl}-2-methoxyphenyl acetate (8)

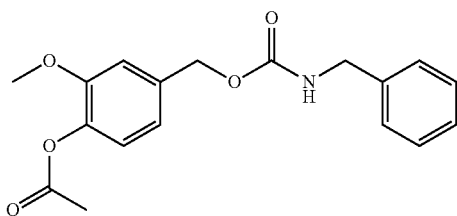 [SMILES: COc1cc(COC(=O)NCc2ccccc2)ccc1OC(C)=O]

Compound VII (339 mg, 0.993 mmol) was dissolved in anhydrous THF (5 mL). To the stirred, yellow solution was added at room temperature a solution of benzylamine (160 mg, 163 pt, 1.5×0.993 mmol) in anhydrous THF (5 mL). After being stirred overnight, the reaction solution was diluted with diethyl ether and extracted with 1N HCl, water and saturated NaCl. The organic phase was dried over anhydrous MgSO$_4$, filtered and concentrated. Purification by column chromatography on silica gel eluting with hexanes/ethyl acetate (7:3-1:1, v/v) afforded 23 mg (7%) of 8 as a clear oil: $R_f$=0.30 (hexanes/ethyl acetate, 1:1, v/v); $^1$HNMR (CDCl$_3$) δ 7.34-7.25 (m, 5H), 6.99 (d, $^3$J=8.0 Hz, 1H), 6.96 (s, 1H), 6.92 (d, $^3$J=8.1 Hz, 1H), 5.09 (s, 2H), 5.04 (bs, 1H, NH), 4.38 (d, $^3$J=6 Hz, 2H), 3.81 (s, 3H) and 2.29 (s, 3H). While the synthesis proceeded in excellent yield, product isolation was compromised by decomposition during work-up.

EXAMPLE 10

4-{[(2-ethylhexylcarbamoyl)oxy]methyl}-2-methoxyphenyl acetate (9)

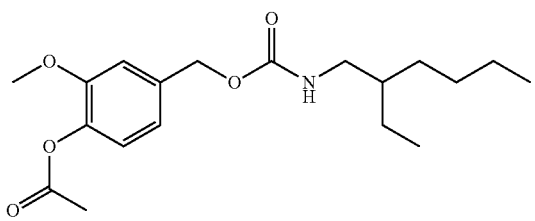 [SMILES: CCCCC(CC)CNC(=O)OCc1ccc(OC(C)=O)c(OC)c1]

To a stirred yellow solution of VII (298.2 mg, 0.873 mmol) in anhydrous THF (10 mL) was added 2-ethylhexylamine (124 mg, 157 μL 1.1×0.873 mmol) and then, dropwise, triethylamine (97 mg, 135 μL, 1.1×0.873 mmol). The solution was stirred for 3 hours at room temperature. The colorless solution was then diluted with diethyl ether and washed with 1N HCl, distilled water, and saturated NaCl. The organic layer was dried over anhydrous MgSO$_4$, filtered, and concentrated. The crude product was purified by column chromatography on silica gel using hexanes/ethyl acetate (6:4, v/v) to give 9 as 207.2 mg (68%) of a clear, light yellow oil: $R_f$=0.60 (hexanes/ethyl acetate, 1:1, v/v); $^1$HNMR (CDCl$_3$) δ 6.99 (d, $^3$J=8.0 Hz, 1H), 6.95 (d, $^4$J=1.75 Hz, 1H), 6.92 (dd, $^3$J=8.0 Hz, 4J=1.72 Hz, 1H), 5.04 (s, 2H), 4.67 (bs, 1H, NH), 3.82 (s, 3H), 3.16-3.08 (m, 2H), 2.29 (s, 3H), 1.43-1.35 (m, 1H), 1.33-1.119 (m, 8H) and 0.867 (apparent triplet, $^3$J=7.2 Hz, 6H). Exact mass (FAB$^+$) calculated for C$_{19}$H$_{30}$NO$_5$ [M+H] 352.2118. found 352.2101.

EXAMPLE 11

4-{[(dodecylcarbamoyl)oxy]methyl}-2-methoxyphenyl acetate (10)

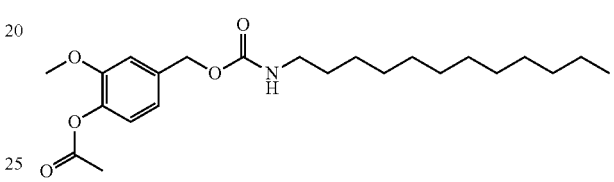

To a stirred yellow solution of VII (290.8 mg, 0.852 mmol) in anhydrous THF (10 mL) was added 1-dodecylamine (174 mg, 1.1×0.852 mmol) and then, dropwise, triethylamine (118 mg, 132 μL, 1.1×0.852 mmol). The solution was stirred for 3.5 hours at room temperature. The colorless solution was then diluted with diethylether and washed with 1N HCl, distilled water, and saturated NaCl. The organic layer was dried over anhydrous MgSO$_4$, filtered, and concentrated. The crude product was purified by column chromatography on silica gel using hexanes/ethyl acetate (6:4, v/v) to give 165 mg (48%) of a white solid, 10: mp=54-56° C. (uncorrected); $R_f$=0.61 (hexanes/ethyl acetate, 1:1, v/v); $^1$HNMR (CDCl$_3$) δ 6.99 (d, $^3$J=8.0 Hz, 1H), 6.95 (d, $^4$J=1.55 Hz, 1H), 6.92 (bd, $^3$J=8.0 Hz, 1H), 5.04 (s, 2H), 4.69 (bs, 1H; NH), 3.82 (s, 3H), 3.17 (apparent quartet, $^3$J=6.7 Hz, 2H), 2.29 (s, 3H), 1.51-1.43 (m, 2H), 1.32-1.19 (m, 18H), and 0.86 (t, $^3$J=7 Hz, 3H). Exact mass (FAB$^+$) calculated for C$_{23}$H$_{38}$NO$_5$ [M+H] 408.2744. found 408.2749.

EXAMPLE 12

2-methoxy-4-({[(2-phenoxyethyl)carbamoyl]oxy}methyl)phenyl acetate (11)

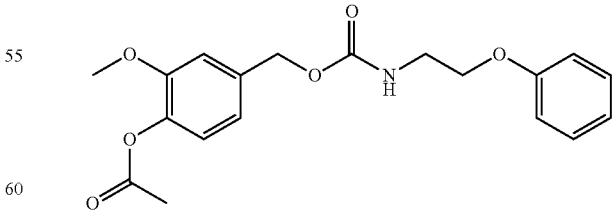

To a stirred yellow solution of VII (371.8 mg, 1.089 mmol) in anhydrous THF (10 mL) was added 2-phenoxyethylamine (165 mg, 157 μL, 1.1×1.089 mmol) and then, dropwise, triethylamine (121 mg, 168 μL, 1.1×1.089 mmol). The solution was stirred for 1.5 hours at room temperature. The colorless solution was then diluted with $CH_2Cl_2$ and washed with 1N HCl, distilled water, and saturated NaCl. The organic layer was dried over anhydrous $MgSO_4$, filtered, and concentrated. The crude product was purified by column chromatography on silica gel using hexanes/ethyl acetate (1:1, v/v) to yield 260.6 mg (67%) of a 11 as a clear light yellow oil: $R_f$=0.39 (hexanes/ethyl acetate, 1:1, v/v); $^1$HNMR (CDCl$_3$) δ 7.26 (td, $^3J$=8.0 Hz, $^4J$=1.1 Hz, 2H), 6.98 (d, $^3J$=8.0 Hz, 1H), 6.96 (m, 1H), 6.94 (d, $^4J$=1.0 Hz, 1H), 6.92 (dd, $^3J$=8.7 Hz, 1H), 6.86 (d, $^3J$=8.1 Hz, 2H), 5.21 (bs, 1H, NH), 5.06 (s, 2H), 4.03 (t, $^3J$=5.0 Hz, 2H), 3.80 (s, 3H), 3.59 (q, $^3J$=5.2 Hz, 2H, NCH$_2$) and 2.29 (s, 3H). Exact mass (EST) calculated for $C_{19}H_{22}NO_6$ [M+H]=360.1442. found 360.1443.

EXAMPLE 13

2-methoxy-4-({[(2-phenylethyl)carbamoyl]oxy}methyl)phenyl acetate (12)

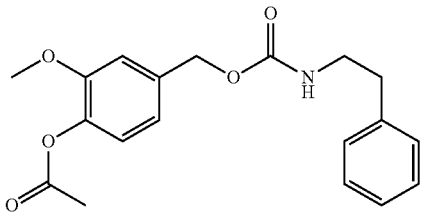 [SMILES: COc1cc(COC(=O)NCCc2ccccc2)ccc1OC(C)=O]

To a stirred yellow solution of VII (362.5 mg, 1.062 mmol) in anhydrous THF (10 mL) was added phenethylamine (142 mg, 147 μL, 1.1×1.062 mmol) and then, dropwise, triethylamine (118 mg, 164 μL, 1.1×1.062 mmol). The solution was stirred for 1 hour at room temperature. The colorless solution was then diluted with $CH_2Cl_2$ and washed with 1N HCl, distilled water, and saturated NaCl. The organic layer was dried over anhydrous $MgSO_4$, filtered, and concentrated. The crude product was purified by column chromatography on silica gel using hexanes/ethyl acetate (1:1, v/v) to yield 203 mg (56%) of 12 as a clear light yellow oil: $R_f$=0.45 (hexanes/ethyl acetate, 1:1, v/v); $^1$HNMR (CDCl$_3$) δ 7.28 (td, $^3J$=7.4 Hz, 2H), 7.20 (tt, $^3J$=7.4 Hz, 1H), 7.16 (d, $^3J$=7.3 Hz, 2H), 6.98 (d, $^3J$=8.0 Hz, 1H), 6.93 (d, 1H), 6.90 (dd, $^3J$=8.0 Hz, 1H), 5.04 (s, 2H, CH$_2$O), 4.73 (bs, 1H, NH), 3.81 (s, 3H, OCH$_3$), 3.45 (q, $^3J$=6.6 Hz, 2H, NCH$_2$), 2.80 (t, $^3J$=6.9 Hz, 2H, PhCH$_2$) and 2.29 (s, 3H). Exact mass (ESI) calculated for $C_{19}H_{22}NO_5$ [M+H]=344.1492. found 344.1496.

EXAMPLE 14

4-({[(cyclohexylmethyl)carbamoyl]oxy}methyl)-2-methoxyphenyl acetate (13)

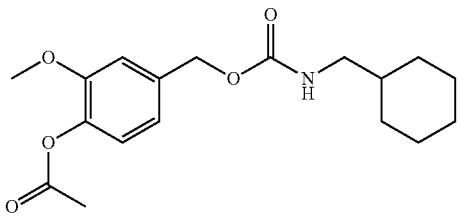 [SMILES: COc1cc(COC(=O)NCC2CCCCC2)ccc1OC(C)=O]

To a stirred yellow solution of VII (293.8 mg, 0.861 mmol) in anhydrous THF (10 mL) was added cyclohexylmethanamine (165 mg, 123 μL, 1.1×0.861 mmol) and then, dropwise, triethylamine (96 mg, 133 μL, 1.1×0.861 mmol). The solution was stirred for 45 minutes at room temperature. The colorless solution was then diluted with $CH_2Cl_2$ and washed with 1N HCl, distilled water, and saturated NaCl. The organic layer was dried over anhydrous $MgSO_4$, filtered, and concentrated. The crude product was purified by column chromatography on silica gel using hexanes/ethyl acetate (1:1, v/v) to yield 150.2 mg (52%) of 13 as a clear colorless oil: $R_f$=0.55 (hexanes/ethyl acetate, 1:1, v/v); $^1$HNMR (CDCl$_3$) δ 6.98 (d, $^3J$=8.0 Hz, 1H), 6.95 (d, 1H), 6.91 (dd, $^3J$=8.0 Hz, 1H), 5.04 (s, 2H, CH$_2$O), 4.75 (bs, 1H, NH), 3.81 (s, 3H, OCH$_3$), 3.01 (t, $^3J$=6.4 Hz, 2H, NCH$_2$), 2.29 (s, 3H), 1.70-1.62 (m, 5H), 1.42 (bs, 1H), 1.23-1.11 (m, 3H) and 0.92 (q, $^3J$=11.5 Hz, 2H).

Exact mass (ESI) calculated for $C_{18}H_{26}NO_5$ [M+H]=336.1805. found 336.1803.

EXAMPLE 15

4-{[(2,3-dihydro-1H-inden-2-ylcarbamoyl)oxy]methyl}-2-methoxyphenyl acetate (14)

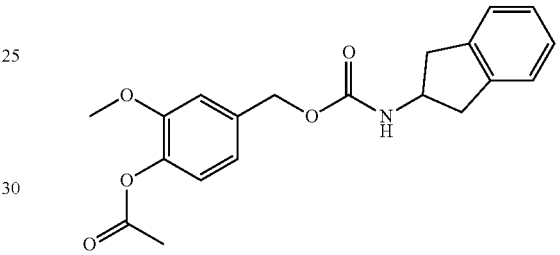

2-Aminoindane hydrochloride (166 mg, 1.1×0.891 mmol) was suspended in solution of VII (304.2 mg, 0.891 mmol) in anhydrous THF (10 mL), triethylamine (198 mg, 275 μL, 2.2×0.891 mmol) was added dropwise, and the reaction mixture was stirred at room temperature for 1 hour. The mixture was diluted with $CH_2Cl_2$ and washed with 1N HCl, distilled water, and saturated NaCl. The organic layer was dried over anhydrous $MgSO_4$, filtered, and concentrated. The crude product was purified by column chromatography on silica gel using hexanes/ethyl acetate (1:1, v/v) to afford 134 mg (42%) white solid, 14: mp=114-116° C. (uncorrected); $R_f$=0.45 (hexanes/ethyl acetate, 1:1, v/v); $^1$HNMR (CDCl$_3$) δ 7.20 (bs, 2H), 7.15 (m, 2H), 6.98 (d, $^3J$=8.0 Hz, 1H), 6.93 (d, 1H), 6.90 (dd, $^3J$=8.0 Hz, 1H), 5.04 (s, 2H, CH$_2$O), 4.51 (bs, 2H), 3.81 (s, 3H, OCH$_3$), 3.28 (dd, $^3J$=16 Hz, $^4J$=7.1 Hz, 2H), 2.80 (dd, $^3J$=16 Hz, $^4J$=4.5 Hz, 2H, NCH$_2$), and 2.29 (s, 3H). Exact mass (ESI) calculated for $C_{20}H_{22}NO_5$ [M+H]=356.1492. found 356.1496.

EXAMPLE 16

4-({[(3,3-dimethylbutyl)carbamoyl]oxy}methyl)-2-methoxyphenyl acetate (16)

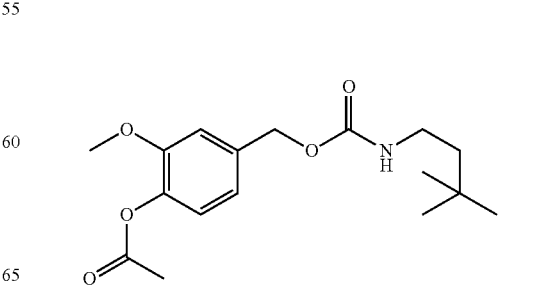

This compound was prepared from VII (288.5 mg, 0.845 mmol), 3,3-dimethylbutylamine (85.5 mg, 114 μL, 0.845 mmol) and anhydrous THF (4.2 mL) as described for 13. The reaction was complete within 2 hours. The reaction solution was diluted with CH$_2$Cl$_2$ and extracted with in 1N HCl and saturated NaCl. The organic layer was dried over anhydrous MgSO$_4$, filtered and concentrated. The crude material was purified by column chromatography on silica gel eluting with hexanes/ethyl acetate (7:3, v/v) to render 95.8 mg (35%) of 16 as an oil; $^1$HNMR (CDCl$_3$) δ 6.99 (d, $^3$J=7.95 Hz, 1H), 6.95 (s, 1H), 6.92 (d, $^3$J=7.95 Hz, 1H), 5.04 (s, 2H), 4.60 (bs, 1H), 3.82 (s, 3H), 3.21-3.17 (m, 2H), 2.29 (s, 3H), 1.42-1.38 (m, 2H) and 0.91-0.90 (m, 9H). Exact mass (ESI) calculated for C$_{17}$H$_{26}$NO$_5$ [M+H]=324.1805. found 324.1814.

EXAMPLE 17

2-methoxy-4-[({[2-(morpholin-4-yl)ethyl]carbamoyl}oxy)methyl]phenyl acetate (17)

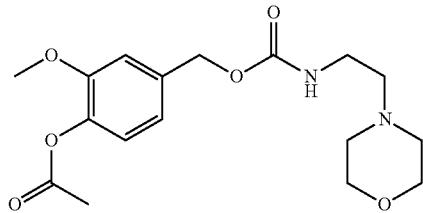 [SMILES: COc1cc(COC(=O)NCCN2CCOCC2)ccc1OC(C)=O]

Compound VII (219.1 mg, 0.642 mmol) was dissolved in anhydrous THF (3.2 mL, 5 mL/mmol of 6). To the yellow solution was added 4-(2-aminoethyl)morpholine (83.5 mg, 84 μL, 0.642 mmol). The reaction solution was stirred for two hours, after which time the solution was colorless. The solvent was removed under reduced pressure. The crude material was purified by column chromatography on silica gel using CH$_2$Cl$_2$/MeOH (96:4, v/v) to give 161 mg (71%) of 17 as a white solid: mp=82-83° C. (uncorrected); R$_f$=0.16 (CH$_2$Cl$_2$/MeOH, 96:4, v/v); $^1$HNMR (CDCl$_3$) δ 6.99 (d, $^3$J=8 Hz, 1H), 6.96 (d, $^4$J=1.65 Hz, 1H), 6.94 (dd, $^3$J=8 Hz, $^4$J=1.8 Hz, 1H), 5.23 (bs, 1H), 5.05 (s, 2H), 3.82 (s, 3H), 3.67 (m, 4H), 3.29 (m, 2H), 2.46 (t, $^3$J=5.9 Hz, 2H), 2.42 (bs, 41-1) and 2.29 (s, 3H). Exact mass (ESI) calculated for C$_{17}$H$_{25}$N$_2$O$_6$ [M+H]=353.1707. found 353.1705.

EXAMPLE 18

4-{[(ethylcarbamoyl)oxy]methyl}-2-methoxyphenyl acetate (18)

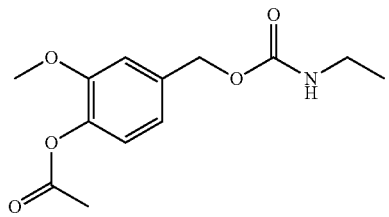 [SMILES: CCNC(=O)OCc1ccc(OC(C)=O)c(OC)c1]

A solution of VII (207 mg, 0.606 mmol), ethylamine (2M in THF, 31.5 mg, H$_2$NEt, 350 μL of solution, 1.16×0.606 mmol H$_2$NEt) and triethylamine (122 mg, 169 μL, 2×0.606 mmol) anhydrous THF (3 mL, 5 mL/mmol of 6) was stirred for one hour. The reaction mixture was diluted with CH$_2$Cl$_2$ and extracted with 1N HCl and saturated NaCl. The organic layer was dried over anhydrous MgSO$_4$, filtered and concentrated. The crude product was purified by column chromatography on silica gel using CH$_2$Cl$_2$/ethyl acetate (94:6, v/v) to give 114.1 mg (70%) of 18 as an oil: R$_f$=0.37 (CH$_2$Cl$_2$/EtOAc, 96:4, v/v); $^1$HNMR (CDCl$_3$) δ 6.98 (d, $^3$J=8 Hz, 1H), 6.95 (bs, 1H), 6.92 (bd, $^3$J=8 Hz, 1H), 5.04 (bs, 2H), 4.68 (bs, 1H), 3.82 (s, 3H), 3.22 (m, 2H) and 1.13 (t, $^3$J=7.25 Hz, 3H). Exact mass (ESI) calculated for C$_{13}$H$_{18}$NO$_5$ [M+H]=268.1179. found 268.1189.

EXAMPLE 19

Ethyl [({[4-(acetyloxy)-3-methoxybenzyl]oxy}carbonyl)amino]acetate (19)

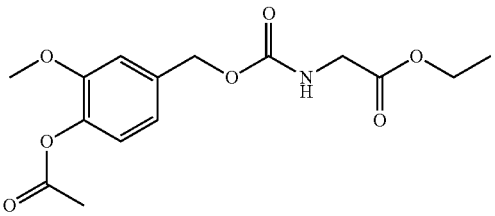 [SMILES: CCOC(=O)CNC(=O)OCc1ccc(OC(C)=O)c(OC)c1]

Thiazolide VII (266.8 mg, 0.781 mmol) was dissolved in anhydrous THF (3 mL), and the resulting solution was added to a previously prepared solution of ethyl glycinate (130 mg, 1.19×0.781 mmol) and diisopropylethylamine (120 mg, 162 μL, 1.19×0.781 mmol) in chloroform (3 mL). To the resulting solution was added triethylamine (72.6 mg, 100 μL, 0.72 mmol) at which point a slight cloudiness developed. The mixture was stirred overnight at room temperature. The reaction mixture was diluted with CH$_2$Cl$_2$ and extracted with 1N HCl and saturated NaCl. The organic layer was dried over anhydrous MgSO$_4$, filtered and concentrated. The product was purified by column chromatography on silica gel using a gradient of CH$_2$Cl$_2$/ethyl acetate (94:6-9:1, v/v) to yield 152.9 mg (60%) of a white solid 19: mp=62-64° C. (uncorrected); R$_f$=0.27 (CH$_2$Cl$_2$/EtOAc, 96:4, v/v); $^1$HNMR (CDCl$_3$) δ 6.99 (d, $^3$J=8 Hz, 1H), 6.96 (bs, 1H), 6.92 (bd, $^3$J=8 Hz, 1H), 5.22 (bs, 1H), 5.08 (bs, 2H), 4.20 (q, $^3$J=7.15 Hz, 2H), 3.96 (d, $^3$J=5.55 Hz, 2H), 3.82 (s, 3H), 2.29 (s, 3H) and 1.27 (t, $^3$J=7.15 Hz, 3H). Exact mass (ESI) calculated for C$_{15}$H$_{20}$NO$_7$ [M+H]=326.1234. found 326.1245.

EXAMPLE 20

Ethyl 2[({[4-(acetoxy)-3-methoxybenzyl]oxy}carbonyl)amino]-3-methylbutanoate (20)

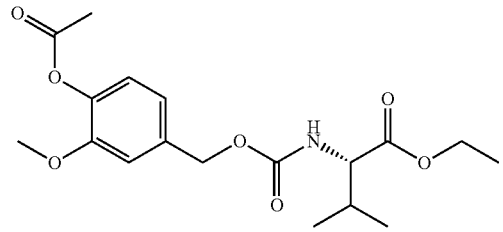 [SMILES: CCOC(=O)[C@@H](NC(=O)OCc1ccc(OC(C)=O)c(OC)c1)C(C)C]

L-Valine ethyl ester hydrochloride (122.5 mg, 1.05×0.642 mmol) and thiazolide VII (219.2 mg, 0.642 mmol) were covered with THF (3.2 mL). To the stirred suspension was added diisopropylethylamine (166 mg, 224 µL, 2×0.642 mmol). The reaction mixture was stirred overnight. A second portion of diisopropylethylamine and four drops of anhydrous methanol were added, and the mixture was stirred for four days. A second portion of portion of valine ethyl ester hydrochloride was added, and the reaction mixture was stirred for two more days, after which time the solution was clear and colorless. The reaction solution was diluted with $CH_2Cl_2$ and extracted with 1N HCl and saturated NaCl. The organic layer was dried over anhydrous $MgSO_4$, filtered, concentrated, and dried well under vacuum. The crude material was covered with four mL of hexanes/ethyl acetate (7:3, v/v) causing the released MTA to separate. The supernatant was drawn of, the crystals rinsed twice with fresh 7:3 hexanes/ethyl acetate, the rinsings were combined with the original supernatant, and the resulting volume concentrated. The product was purified by column chromatography on silica gel using hexanes/ethyl acetate (7:3, v/v) as eluant to give 165.8 mg (71%) of a colorless oil: $R_f$=0.36 (hexanes/ethyl acetate, 7:3, v/v); $^1$HNMR ($CDCl_3$) δ 6.99 (d, $^3J$=8 Hz, 1H), 6.96 (s, 1H), 6.92 (bd, $^3J$=8 Hz, 1H), 5.26 (d, 8.15 Hz, 1H), 5.06 (s, 2H), 4.28-4.24 (m, 1H), 4.23-4.15 (m, 2H), 3.82 (s, 3H), 2.29 (s, 3H), 2.18-2.11 (m, 1H), 1.26 (t, $^3J$=7 Hz, 3H), 0.95 (d, $^3J$=6.8 Hz, 3H) and 0.88 (d, 6.8 Hz, 3H). Exact mass (ESI) calculated for $C_{18}H_{25}NO_7Na$ [M+Na]=390.1523. found 390.1515.

REFERENCES

Abouabdellah A, et al., "Derivatives of piperidinyl- and piperazinyl-alkyl carbamates, preparation methods thereof and application of the same in therapeutics," U.S. Pat. No. 7,214,798 B2, May 8, 2007.

A'Court R, Fox W J, Hamlin J E, et al., "Carbamates: production and use as fuel additives," U.S. Pat. No. 5,126,477, Jun. 30, 1992.

Ahluwalia J, Yaqoob M, Urban L, et al., "Activation of capsaicin-sensitive primary sensory neurones induces anandamide production and release," *J. Neurochem.*, 84: 585-591 (2003).

Boger D L, Sato H, Lerner A E, et al., "Exceptionally potent inhibitors of fatty acid amide hydrolase: The enzyme responsible for degradation of endogenous oleamide and anandamide," *Proc Natl Acad Sci USA* 97 5044-5049 (2000).

Boger D L, "Inhibitors of fatty acid amide hydrolase," U.S. Pat. No. 6,462,054 B1, Oct. 8, 2002.

Casillas R P, Mitcheltree L W, and Stemler F W, "The mouse ear model of cutaneous sulfur mustard injury." *Toxicol. Methods* 7, 381-397 (1997).

Casillas R P, Kiser R C, Truxall J A, Singer A W, Shumaker S M, Niemuth N A, Ricketts K M, Mitcheltree L W, Castrejon L R, Blank J A, "Therapeutic approaches to dermatotoxicity by sulfur mustard. I. Modulaton of sulfur mustard-induced cutaneous injury in the mouse ear vesicant model." *J Appl Toxicol* 20 Suppl 1: S145-51 (2006).

Cortright D N., Szallasi A., "TRP Channels and Pain," *Curr Pharm Des.* 15: 1736-1749 (2009).

Cravatt B F, Demarest K, Patricelli M O, et al., "Supersensitivity to anandamide and enhanced endogenous cannabinoid signaling in mice lacking fatty acid amide hydrolase," *PNAS*, 98: 9371-9376 (2001)

Dasse O, "Combination FAAH inhibitor and analgesic, anti-inflammatory or anti-pyretic agents," PCT, WO 2008/021625 A2, Feb. 21, 2008, Dasse O, Putman D, Compton T R, Parrott J A, "Metabolically-stabilized inibitors of fatty acid amide hydrolase," PCT, WO 2008/063714 A1, May 29, 2008.

De Petrocellis L, Di Marzo V., "Role of endocannabinoids and endovanilloids in Ca2+ signaling" *Cell Calcium* 45(6): 611-624 (2009).

Dinh T P, Carpenter D., Leslie F M, et al., "Brain monoglyceride lipase participating in endocannabinoid inactivation," *Proc Natl Acad Sci USA* 99 (16) 10819-10824 (2002).

Fowler C J, Naidu P S, Lichtman A, et A, "The case for the development of novel analgesic agents targeting both fatty acid amide hydrolase and either cyclooxygenase or TRPV1," Br. J. Pharmacol., 56 (3): 412-419 (2009)

Gilula N B, Cravatt B F, and Lerner R A, "Fatty-acid amide hydrolase," U.S. Pat. No. 7,348,173 B2, Mar. 25, 2008

Guo A., Vulchanova L., Wang J, et al., Immunocytochemical localization of the vanilloid receptor 1 (VR1): relationship to neuropeptides, the P2X3 purinoceptor and IB4 binding sites, *Eur. J. Neurosci.* 11: 946-958 (1999)

Huang M-T, Smart R C, Wong C-Q, and Conney A H, "Inhibitor effect of curcumin, chlorogenic acid, caffeic acid, and ferulic acid on tumor promotion in mouse skin by 12-O-tetradecanoylphorbol-13-acetate." Cancer Res. 48: 5941-5946 (1988)

Huang M-T, Ho C-T, Wang Z Y, Ferraro T, Lou Y R, Stauber K, Ma W, Georgiadis C, Laskin J D and Conney A H, "Inhibition of skin tumorigenesis by rosemary and its constituents carnosol and ursolic acid," Cancer Res, 54: 701-708 (1994).

Kondo S, Kondo H., Nakane S., et al., "2-Arachidonoylglycerol, an endogenous cannabinoid receptor agonist: Identification as one of the major species of monoacylglycerols in various rat tissues, and evidence for its generation through $Ca^{2+}$-dependent and -independent mechanisms," *FEBS Lett* 429: 152-156 (1998).

Lambert D M, Fowler C J, "The endocannabinoid system: Drug targets, lead compounds, and potential therapeutic applications," *J Med Chem* 48(16): 5059-5087 (2005).

Messeguer A, Planells-Cases R, Ferrer-Montiel A, "Physiology and pharmacology of the vanilloid receptor," *Curr Neuropharmacol.*, 4 (1): 1-15 (2006)

Mouslech Z, Valla V, "Endocannabinoid system: an overview of its potential in current medical practice," *Neuro Endocrinol Lett.* 30(2):153-179 (2009)

Nagao Y, Seno K, Kawabata K, et al., "Monitored aminolysis of 3-acylthiazolidine-2-thione: a new convenient synthesis of amide," *Tetrahedron Letters*, 21, 841-844 (1980).

Nagao Y, Miyasaka T., Seno K., et al., "Monitored aminolysis of 3-acyl-1,3-thiazolidine-2-thione with amino acid and its derivative: peptide bond formation, chemselective acylation and bridging reaction," *Chemistry Letters*, 463-466 (1981).

Nagele E., Schelhaas M., Kuder N., et al., "Chemoenzymatic syntheses of N-Ras lipopeptides," *J. Am Chem. Soc.*, 120: 6889-6902 (1998)

Premkumar, L S, Ahern G P, "Induction of vanilloid receptor channel activity by protein kinase C, *Nature*, 408: 985-990 (2000)

Richardson J D, Kilo S, Hargreaves K M "Cannabinoids reduce hyperalgesia and inflammation via interaction with peripheral $CB_1$ receptors," *Pain*, 75: 111-119 (1998).

Rodriguez De Fonseca F, Del Arco I., Bermudez-Silva F., et al., "The endocannabinoid system: physiology and pharmacology," *Alcohol & Alcoholism* 40(1): 2-14 (2005).

Ross R A, "Anandamide and vanilloid TRPV1 receptors," *Brit. J. Pharmacology*, 140: 790-801 (2003)

Szallasi A., Appendino G., "Vanilloid receptor TRPV1 antagonists as the next generation of painkillers. Are we putting the cart before the horse?," *J. Med. Chem.* 47: 2717-2723 (2004).

Schlosburg J E, Kinsey S G, Lichtman A H, "Targeting fatty acid amide hydrolase (FAAH) to treat pain and inflammation," AAPS J. 11(1):39-44 (2009)

Seierstad M, Breitenbucher J G., "Discovery and development of fatty acid amide hydrolase (FAAH) inhibitors," J Med. Chem. 51(23):7327-7343 (2008).

Swanson D M, Dubin A E, Shah C, et al., "Identification and biological evaluation of 4-(3-trifluoromethylpyridin-2-yl) piperazine-1-carboxylic acid (5-trifluoromethylpyridin-2-yl)amide, a high affinity TRPV1 (VR1) vanilloid receptor antagonist," *J Med. Chem.*, 48(6):1857-1872 (2005).

Staab H A, "New methods of preparative organic chemistry IV. Syntheses using heterocyclic amides (azolides), *Angew Chem Intern Ed English,* 1(7): 351 (1962).

Stella N, Schweitzer P, Piomelli D, "A second endogenous cannabinoid that modulates long-term potentiation," *Nature* 388 773-778 (1997).

Sugiura T, Kodaka T, Nakane S, et al., "Evidence that the cannabinoid $CB_1$ receptor is a 2-arachidonoylglycerol receptor. Structure-activity relationship of 2-arachidonoylglycerol, ether-linked analogues, and related compounds," *J Biol. Chem.*, 274: 2794-2801 (1999), van der Stelt M., DiMarzo V., "Endovanilloids—Putative endogenous ligands of transient receptor potential vainoolid 1 channels," *Eur. J. Biochem.*, 271: 1827-1834 (2004).

Vandevoorde S, "Overview of the chemical families of fatty acid amide hydrolase and monoacylglycerol lipase inhibitors," *Curr Top Med. Chem.*, 8 (3): 247-267 (2008).

Verma R K, Garg S, "Selection of Excipients for Extended Release," *Journal of Pharmaceutical and Biomedical Analysis,* 38 (4): 633-644 (2005)

Walker K M, Urban L, Medhurst S J, et al., "The VR1 antagonist capsazepine reverses mechanical hyperalgesia in models of inflammatory and neuropathic pain," Pharmacol Exp Ther., 304:56-62 (2003).

World Health Organization, "Carbamate Pesticides," *Environmental Health Criteria* #64, Geneva, Switzerland (1986).

Zimov S, Yazulla S, "Vanilloid receptor 1 (TRPV1/VR1) co-localizes with fatty acid amide hydrolase (FAAH) in retinal amacrine cells." *Visual Neuroscience,* 24: 581-591 (2007).

It should be understood that this specification and examples are set forth by way of illustration and not limitation and that various modifications and changes may be made without departing from the spirit and scope of the present invention as defined by the appended claims.

We claim:
1. The Compound of the formula (I)

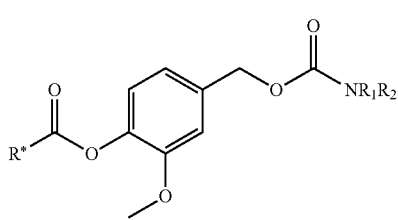

wherein
$R_1$, $R_2$, and R* are hydrogen, $(C_1-C_{15})$alkyl, $(C_1-C_{15})$alkyl $(C_1-C_6)$alkoxy, aryl, $(C_3-C_6)$cycloalkyl, $(C_3-C_6)$cycloalkyl-$(C_1-C_6)$alkyl, $(C_1-C_6)$alkaryl, heterocyclic, $(C_1-C_6)$alkyl heterocyclic, and amino acyl and pharmaceutically acceptable addition salts thereof and optical and geometric isomers or racemic mixtures thereof.

2. The compound of claim 1 wherein
$R_1$ and $R_2$ are alike or different and selected from hydrogen, $(C_1-C_{15})$alkyl, $(C_1-C_{15})$alkyl$(C_1-C_6)$alkoxy, aryl, $(C_3-C_6)$cycloalkyl, $(C_3-C_6)$cycloalkyl-$(C_1-C_6)$alkyl, $(C_1-C_6)$alkaryl, heterocyclic, $(C_1-C_6)$alkyl heterocyclic, and amino acyl;
R* is $(C_1-C_6)$alkyl or aryl; and
pharmaceutically acceptable acid addition salts thereof and optical and geometric isomers or racematic mixtures thereof.

3. The compound of claim 2 wherein
$R_1$ is hydrogen $(C_1-C_{15})$alkyl;
$R_2$ is hydrogen $(C_1-C_{15})$alkyl, $(C_1-C_{15})$alkyl$(C_1-C_6)$ alkoxy, aryl, $(C_3-C_6)$cycloalkyl, $(C_3-C_6)$cycloalkyl-$(C_1-C_6)$alkyl, $(C_1-C_6)$alkaryl, heterocyclic, $(C_1-C_6)$alkyl heterocyclic, and amino acyl; and
R* is $(C_1-C_6)$alkyl.

4. The compound of the formula (I)

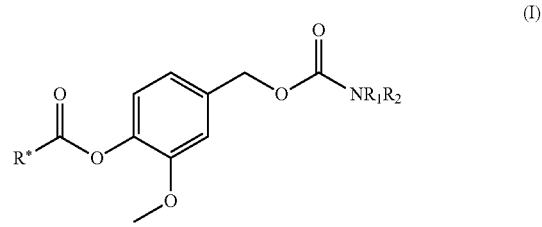

wherein
$R_1$ is hydrogen or n-butyl;
$R_2$ is ethyl, n-butyl, n-hexyl, n-octyl, n-heptyl, 2ethylhexyl, n-dodecyl, cyclohexyl, cyclohexylmethyl, 2-phenoxyethyl, phenethyl, 2-indanyl, 2-methoxyethyl, 33-dimethylbutyl, 2-(4-morpholino)ethyl, ethyl 2-glycinyl or ethyl 2-valinyl; and
R* is methyl.

5. The compound which is
4-{[(cyclohexylcarbamoyl)oxy]methyl}-2-methoxyphenyl acetate,
4-{[(butylcarbamoyl)oxy]methyl}-2-methoxyphenyl acetate,
4-{[(hexylcarbamoyl)oxy]methyl}-2-methoxyphenyl acetate,
4-{[(octylcarbamoyl)oxy]methyl}-2-methoxyphenyl acetate,
4-{[(decyclacarbamoyl)oxy]methyl}-2-methoxyphenyl acetate,
2-methoxy-4-({[(2-methoxyethyl)carbamoyal] oxy}methyl)phenyl acetate,
4-(acetyloxy)-3-methoxybenzyl 2-thioxo-13 thiazolidine-3carboxylate,
4-{[(heptylcarbamoyl)oxy]methyl}-2methoxyphenyl acetate,
4-{[(dibutylcarbamoyl)oxy]methyl}-2-methoxyphenyl acetate,
4-{[(benzylcarbamoyl)oxy]methyl}-2-methoxyphenyl acetate, 4-{[(2-ethylhexycarbamoyl)oxy]methyl}-2-methoxyphenyl acetate 4-{[(dodecylcarbamoyl)oxy]methyl}-2-methoxyphenyl acetate, 2-methoxy-4-({[(2-phenoxyethyl)carbamoyal]oxy}methyl)phenyl acetate, 2-methoxy-4-({[(2-phenylethyl)carbamoyal]oxy}methyl)phenyl acetate, 4-({[(cyclohexylmethyl)carbamoyl]oxy}methyl)-2-methoxyphenyl acetate 4-{[(2,3-dihydro-1H-inden-2-ylcarbamoyl)oxy]methyl}-2-methoxyphenyl acetate, 4-({[(3,3-dimethylbutyl)carbamoyl]oxy}methyl)-2-methoxyphenyl acetate, 2-methoxy-4-[({[2-(morpholin-4-yl)ethyl]carbamoyl}oxy)methyl]phenyl acetate, 4-{[(ethylcarbamoyl)oxy]methyl}-2-methoxyphenyl acetate, ethyl 2[({[4-(acetyloxy)-3-methoxybenzyl]oxy}carbonyl)amino]acetate, or ethyl 2[({[4-(acetoxy)-3-methoxybenzyl]oxy}carbonyl)amino]-3-methylbutanoate.

6. A pharmaceutical composition which comprises a pharmaceutically acceptable carrier and a pharmaceutically effective amount of claim 1.

7. A method of treating Alzheimer's dementia, Parkinson's disease, depression, pain, rheumatoid arthritis, multiple sclerosis, or inflammation which comprises administering to a patient an effective amount of the compound of claim 1.

8. A method of treating Huntington's disease, hypertension, arthritis, allergic airway inflammation, Crohn's disease, ulcerative colitis, or neuropathic pain which comprises administering to a patient an effective amount of the compound of claim 1.

9. A method of preparing a compound of formula (I)

(I)

wherein
$R_1$ is hydrogen;
$R_2$ is n-butyl, n-hexyl, n-octyl or cyclohexyl; and
R* is methyl, which comprises
reacting a benzyl alcohol compound of formula (I)

(a)

with an isocyanate of formula (b)

RNCO (b)

wherein
R is n-butyl, n-hexyl, n-octyl or cyclohexyl;
and obtaining the compound of formula (I).

10. A method of preparing a compound of formula (I)

(I)

wherein
$R_1$, $R_2$, and R* are hydrogen, $(C_1-C_{15})$alkyl, $(C_1-C_{15})$alkyl $(C_1-C_6)$alkoxy, aryl, $(C_3-C_6)$cycloalkyl, $(C_3-C_6)$cycloalkyl-$(C_1-C_6)$alkyl, $(C_1-C_6)$alkaryl, heterocyclic, $(C_1-C_6)$alkyl heterocyclic, and amino acyl and pharmaceutically acceptable addition of salts thereof and optical and geometric isomers or racemic mixtures thereof, which comprises reacting a benzyl alcohol compound of formula (a)

(a)

with carbonyldiimidazole (CDI) of formula (c)

CDI (c) to obtain the compound of formula (d)

(d)

reacting the compound of formula (d) with $NHR_1R_2$ and obtaining the compound of formula (I).

11. A method of preparing a compound of formula (I)

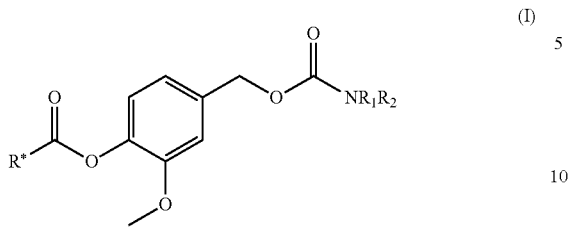

wherein, $R_1$, $R_2$ and $R^*$ are hydrogen, $(C_1-C_{15})$alkyl, $(C_{1-15})$alkyl$(C_1-C_6)$alkoxy, aryl, $(C_3-C_6)$cycloalkyl, $(C_3-C_6)$cycloalkyl-$(C_1-C_6)$alkyl, $(C_1-C_6)$alkaryl, heterocyclic, $(C_1-C_6)$alkyl heterocyclic, and amino acyl and pharmaceutically acceptable addition of salts thereof and optical and geometric isomers or racemic mixtures thereof, which comprises reacting a benzyl alcohol compound of formula (a)

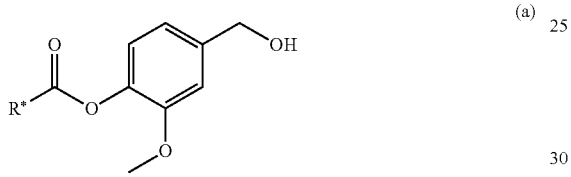

with N-chloroformylthiazolidine-2-thione of formula (e)

to obtain the compound of formula (f)

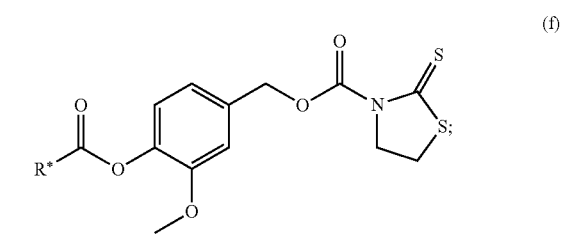

reacting the compound of formula (f) with $NHR_1R_2$ and obtaining the compound of formula (I).

* * * * *